US009265406B2

(12) United States Patent
Takei et al.

(10) Patent No.: US 9,265,406 B2
(45) Date of Patent: Feb. 23, 2016

(54) ENDOSCOPE APPARATUS

(71) Applicant: OLYMPUS MEDICAL SYSTEMS CORP., Tokyo (JP)

(72) Inventors: Shunji Takei, Hachioji (JP); Nobuyuki Doguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/291,112

(22) Filed: May 30, 2014

(65) Prior Publication Data

US 2014/0267657 A1 Sep. 18, 2014

Related U.S. Application Data

(63) Continuation of application No. PCT/JP2013/061893, filed on Apr. 23, 2013.

(30) Foreign Application Priority Data

May 1, 2012 (JP) .................................. 2012-104831

(51) Int. Cl.
*A61B 1/04* (2006.01)
*A61B 1/06* (2006.01)
(Continued)

(52) U.S. Cl.
CPC ........... *A61B 1/00009* (2013.01); *A61B 1/0002* (2013.01); *A61B 1/00186* (2013.01); *A61B 1/043* (2013.01); *A61B 1/045* (2013.01); (Continued)

(58) Field of Classification Search
None
See application file for complete search history.

(56) References Cited

U.S. PATENT DOCUMENTS 5,001,556 A * 3/1991 Nakamura et al. ............... 348/70
2002/0175993 A1 * 11/2002 Ueno et al. ...................... 348/68
(Continued)

FOREIGN PATENT DOCUMENTS

EP 2 047 792 A1 4/2009
EP 2 404 544 A1 1/2012
(Continued)

OTHER PUBLICATIONS

Japanese Office Action dated Oct. 8, 2013 in Japanese Patent Application No. 2013-533799.
(Continued)

*Primary Examiner* — Jorge L Ortiz Criado
*Assistant Examiner* — Samuel D Fereja
(74) *Attorney, Agent, or Firm* — Scully, Scott, Murphy & Presser, PC

(57) ABSTRACT

An endoscope apparatus includes: an image pickup portion that, with respect to return light including a plurality of wavelength band components that is generated accompanying irradiation of illuminating light onto an object, receives the return light with a plurality of different spectral sensitivities and generates an image pickup signal for each of the spectral sensitivities; a correction portion that, based on a spectral distribution of the return light and spectral sensitivity characteristics of the image pickup portion, sets a correction coefficient so that spectral distributions for each of the plurality of wavelength band components included in the image pickup signals become a similar shape to each other; and a calculation portion that, based on the correction coefficient, performs a calculation that separates image pickup signals into each wavelength band component among the plurality of wavelength band components included in the return light.

3 Claims, 9 Drawing Sheets

(51) Int. Cl.
  *A61B 1/00*    (2006.01)
  *G02B 23/24*   (2006.01)
  *A61B 1/045*   (2006.01)
  *A61B 5/00*    (2006.01)
  *H04N 5/217*   (2011.01)
  *H04N 9/04*    (2006.01)
  *G02B 27/10*   (2006.01)
  *H04N 5/225*   (2006.01)

(52) U.S. Cl.
  CPC ............... *A61B1/06* (2013.01); *A61B 1/0638* (2013.01); *A61B 5/489* (2013.01); *G02B 23/2469* (2013.01); *H04N 5/2173* (2013.01); *H04N 5/2256* (2013.01); *H04N 9/045* (2013.01); *A61B 1/0684* (2013.01); *G02B 27/102* (2013.01); *H04N 2005/2255* (2013.01)

(56) References Cited

U.S. PATENT DOCUMENTS

| | | | |
|---|---|---|---|
| 2005/0027166 A1* | 2/2005 | Matsumoto et al. | 600/162 |
| 2005/0234302 A1* | 10/2005 | MacKinnon et al. | 600/181 |
| 2007/0016077 A1* | 1/2007 | Nakaoka et al. | 600/476 |
| 2007/0102623 A1* | 5/2007 | Fengler et al. | 250/208.1 |
| 2009/0124854 A1 | 5/2009 | Yamaguchi et al. | |
| 2009/0141125 A1 | 6/2009 | Yamazaki | |
| 2011/0149057 A1* | 6/2011 | Beck et al. | 348/65 |
| 2012/0010465 A1 | 1/2012 | Erikawa et al. | |
| 2012/0127293 A1 | 5/2012 | Yamazaki | |
| 2012/0215066 A1 | 8/2012 | Akiyama et al. | |

FOREIGN PATENT DOCUMENTS

| | | |
|---|---|---|
| EP | 2 537 456 A1 | 12/2012 |
| JP | 2008-036035 A | 2/2008 |
| JP | 2012016545 A | 1/2012 |
| JP | 5076036 B2 | 11/2012 |
| WO | WO 2008/015826 A1 | 2/2008 |
| WO | 2011162099 A1 | 12/2011 |
| WO | WO 2011/162111 A1 | 12/2011 |

OTHER PUBLICATIONS

International Search Report dated May 21, 2013 issued in PCT/JP2013/061893.

Extended Supplementary European Search Report dated Jul. 23, 2015 from related European Application No. 13 78 5225.7.

* cited by examiner

ENDOSCOPE APPARATUS

CROSS REFERENCE TO RELATED APPLICATION

This application is a continuation application of PCT/JP2013/061893 filed on Apr. 23, 2013 and claims benefit of Japanese Application No. 2012-104831 filed in Japan on May 1, 2012, the entire contents of which are incorporated herein by this reference.

BACKGROUND OF THE INVENTION

1. Field of the Invention

The present invention relates to an endoscope apparatus, and more particularly to an endoscope apparatus that picks up an image of light that includes a plurality of wavelength band components.

2. Description of the Related Art

Endoscope apparatuses have been conventionally used in a medical field for purposes such as observing the inside of a body cavity of a subject. More specifically, an endoscope apparatus used in the medical field has a configuration that, for example, includes a light source apparatus that supplies an illuminating light that is irradiated onto a site to be observed inside a body cavity, an endoscope that picks up an image of return light that is generated accompanying irradiation of the illuminating light onto the site to be observed inside the body cavity, and an image processing apparatus that generates an image of the site to be observed based on the return light for which an image was picked up by the endoscope.

Further, many endoscope apparatuses having the above described configuration adopt an image pickup method that is one of a frame-sequential image pickup method and a simultaneous image pickup method.

More specifically, the aforementioned frame-sequential image pickup method can be realized, for example, by a configuration in which an image of return light that is generated when frame-sequential light obtained by subjecting illuminating light including a plurality of wavelength band components to time division is irradiated onto a site to be observed is picked up by an image pickup device in which a color filter is not provided on an image pickup surface.

The aforementioned simultaneous image pickup method can be realized, for example, by a configuration in which an image of return light that is generated when illuminating light including a plurality of wavelength band components is irradiated onto a site to be observed is picked up by an image pickup device in which a color filter in which a plurality of minute filters that are each equipped with a predetermined spectral sensitivity characteristic are disposed in a predetermined arrangement is provided on an image pickup surface.

For example, Japanese Patent Application Laid-Open Publication No. 2008-036035 discloses an endoscope apparatus that adopts the aforementioned simultaneous image pickup method.

In this connection, generally, each filter included in the aforementioned color filter is configured to have a spectral sensitivity characteristic that transmits not only light of a predetermined color component, but also light of a wide band from a visible region to a near-infrared region.

More specifically, for example, an R filter included in a common Bayer array RGB color filter is configured to have a spectral sensitivity characteristic that transmits not only red light but also a part of blue light and green light.

SUMMARY OF THE INVENTION

An endoscope apparatus according to one aspect of the present invention includes: an image pickup portion that, with respect to return light including a plurality of wavelength band components that is generated accompanying irradiation of illuminating light onto an object, receives the return light with a plurality of different spectral sensitivities and generates an image pickup signal for each of the spectral sensitivities; a correction portion that, based on information relating to a spectral distribution of the return light that is generated from the object and information showing spectral sensitivity characteristics of the image pickup portion, sets a correction coefficient so that spectral distributions for each of the plurality of wavelength band components included in the image pickup signals generated by the image pickup portion become a similar shape to each other; and a calculation portion that, based on the correction coefficient that is set by the correction portion, performs a calculation that separates image pickup signals for each of the spectral sensitivities generated by the image pickup portion into each wavelength band component among the plurality of wavelength band components included in the return light.

DETAILED DESCRIPTION OF THE PREFERRED EMBODIMENT(S)

An embodiment of the present invention will be described hereunder with reference to the drawings.

Figure 1:
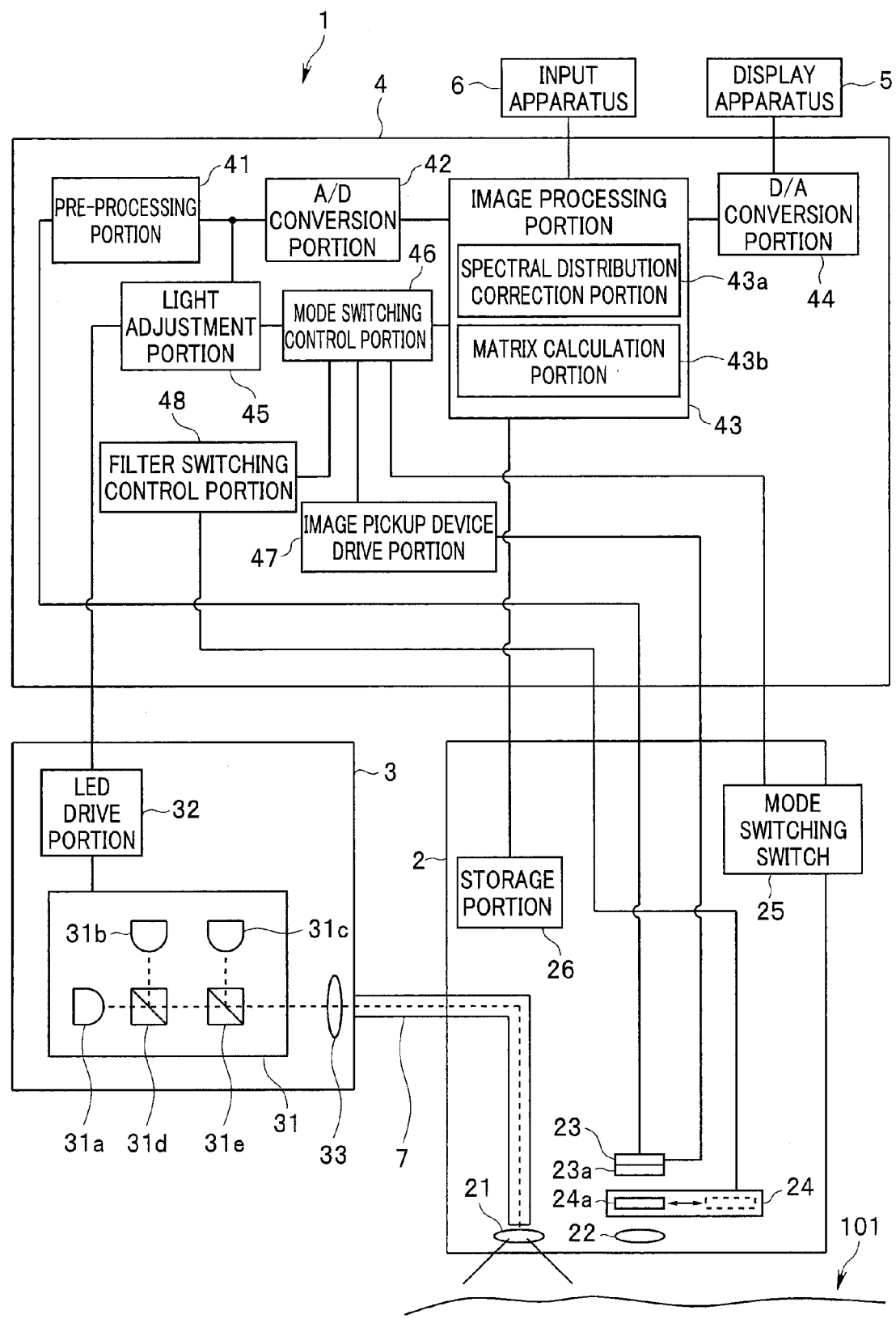
FIG. 1 is a view illustrating a configuration of main components of an endoscope apparatus according to an embodiment of the present invention.

FIG. 1 to FIG. 6 relate to an embodiment of the present invention. FIG. 1 is a view illustrating a configuration of main components of an endoscope apparatus according to an embodiment of the present invention.

As shown in FIG. 1, an endoscope apparatus 1 includes: a scope 2 that can be inserted into a body cavity of a subject and that is configured so as to pick up an image of an object such as living tissue that is present inside the body cavity to acquire image data; a light source apparatus 3 configured to supply illuminating light that is to be emitted towards the object to the scope 2; a processor 4 configured to generate and output a video signal corresponding to the image data acquired by the scope 2; a display apparatus 5 configured to display an image corresponding to the video signal outputted from the processor 4; and an input apparatus 6 having a function as an information input portion that enables the input of information and the like to the processor 4 in accordance with a user operation. Further, a light guide 7 configured to transmit the light supplied from the light source apparatus 3 to a distal end portion of the scope 2 is inserted through the inside of the scope 2.

The scope 2 is configured as an endoscope that includes, for example, an elongated insertion portion and includes, at a distal end portion thereof, an illumination optical system 21 that emits illuminating light transmitted by the light guide 7 onto an object, an objective optical system 22 that forms an image of return light from the object that was illuminated with the illuminating light, an image pickup device 23 in which an image pickup surface is disposed at an image forming position of the objective optical system 22, a color filter 23a attached to the image pickup surface of the image pickup device 23, and a filter switching apparatus 24 disposed in an optical path between the objective optical system 22 and the color filter 23a.

The scope 2 also includes a mode switching switch 25 capable of issuing an instruction relating to switching of an observation mode of the endoscope apparatus 1, and a storage portion 26 in which predetermined information that is used for image processing performed by the processor 4 is stored in advance.

The image pickup device 23 is configured to be driven based on an image pickup device drive signal outputted from the processor 4, to thereby pick up an image of an object, generate an image pickup signal corresponding to the picked up image of the object and output the image pickup signal to the processor 4.

Figure 2:
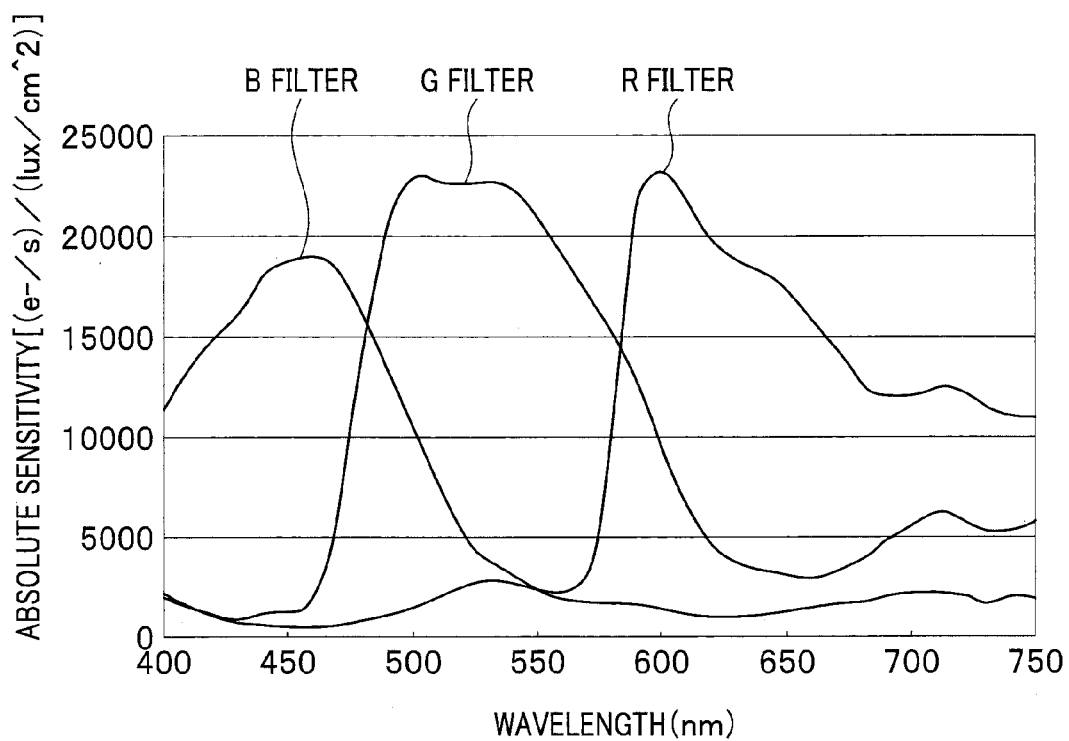
FIG. 2 is a view illustrating an example of spectral sensitivity characteristics of an R filter, a G filter, and a B filter provided in a color filter of the endoscope apparatus illustrated in FIG. 1.

The color filter 23a is formed by arranging a plurality of filters, namely, R (red) filters, G (green) filters, and B (blue) filters, that are respectively provided with predetermined spectral sensitivity characteristics (optical characteristics) in a Bayer array (in a checkerboard pattern) at positions corresponding to respective pixels of the image pickup device 23. Note that in the present embodiment, it is assumed that, for example, R filters, G filters and B filters having the spectral sensitivity characteristics shown in FIG. 2, respectively, are provided in the color filter 23a. FIG. 2 is a view illustrating an example of the spectral sensitivity characteristics of each R filter, G filter and B filter provided in the color filter of the endoscope apparatus shown in FIG. 1.

The R filter of the color filter 23a is configured to have spectral sensitivity characteristics (optical characteristics) such that transmittance in a range from a red region to a near-infrared region becomes relatively higher than transmittances in the other wavelength bands (see FIG. 2). That is, the R filter of the color filter 23a is configured such that transmittance in the wavelength band of FL light which will be described later becomes relatively higher than transmittances in the other wavelength bands.

The G filter of the color filter 23a is configured to have spectral sensitivity characteristics (optical characteristics) such that transmittance in a green region becomes relatively higher than transmittances in the other wavelength bands (see FIG. 2). That is, the G filter of the color filter 23a is configured such that transmittance in the wavelength band of REF light which will be described later becomes relatively higher than transmittances in the other wavelength bands.

The B filter of the color filter 23a is configured to have spectral sensitivity characteristics (optical characteristics) such that transmittance in a blue region becomes relatively higher than transmittances in the other wavelength bands (see FIG. 2).

The filter switching apparatus 24 is configured to perform an operation to retract an excitation light cut filter 24a from an optical path between the objective optical system 22 and the color filter 23a upon detecting that the endoscope apparatus 1 has been switched to a white light observation mode based on a filter switching signal outputted from the light source apparatus 3. Further, when the excitation light cut filter 24a is retracted from the optical path between the objective optical system 22 and the color filter 23a, the filter switching apparatus 24 is configured to transmit light in each wavelength band incident via the objective optical system 22 to the color filter 23a side.

On the other hand, the filter switching apparatus 24 is configured to perform an operation to interpose the excitation light cut filter 24a into the optical path between the objective optical system 22 and the color filter 23a upon detecting that the endoscope apparatus 1 has been switched to a fluorescence observation mode based on a filter switching signal outputted from the light source apparatus 3.

Further, when the excitation light cut filter 24a is interposed into the optical path between the objective optical system 22 and the color filter 23a, the filter switching apparatus 24 is configured so as to transmit to the color filter 23a side only light in a predetermined wavelength band corresponding to the optical characteristics of the excitation light cut filter 24a from among the light in each wavelength band incident via the objective optical system 22. More specifically, the excitation light cut filter 24a is configured to have optical characteristics such that, for example, the excitation light cut filter 24a blocks NBX light which is described later (transmittance of NBX light is set to approximately 0) and substantially transmits light in wavelength bands other than the wavelength band of the NBX light.

The mode switching switch 25 is configured to be able to issue an instruction for switching the observation mode of the endoscope apparatus 1 to any one observation mode selected from the white light observation mode and the fluorescence observation mode in accordance with an operation by a surgeon or the like.

The storage portion 26 is constituted by a non-volatile memory or the like. Predetermined information that is used for calculation processing for acquiring a matrix MAUA which is described later is previously stored in the storage portion 26. The storage portion 26 is configured to output the predetermined information to the processor 4 when it is detected that the scope 2 and the processor 4 are connected. Note that the predetermined information stored in the storage portion 26 will be described in detail later.

The light source apparatus 3 includes an LED light source portion 31, an LED drive portion 32, and a condensing optical system 33 that condenses light emitted from the LED light source portion 31 and supplies the condensed light to the light guide 7.

The LED light source portion 31 is configured to include an LED 31a that emits WB light that is wide-band light, an LED 31b that emits NBX light that is narrow-band light, an LED 31c that emits NBR light that is narrow-band light, an optical element 31d, and an optical element 31e.

The LED 31a includes, for example, a white LED and is configured so as to be capable of emitting white light as the WB light.

The LED 31b is configured to be capable of emitting light in a wavelength band that includes an excitation wavelength of a predetermined fluorescent substance such as a fluorescent probe as the NBX light.

The LED 31c is configured to be capable of emitting, as the NBR light, light in a wavelength band that does not overlap with the NBX light.

The optical element 31d is constituted by, for example, a half mirror, and has optical characteristics such that the WB light emitted from the LED 31a is transmitted to the optical element 31e side and the NBX light emitted from the LED 31b is reflected toward the optical element 31e side.

The optical element 31e is constituted by, for example, a half mirror, and has optical characteristics such that the WB light and NBX light emitted via the optical element 31d are transmitted to the condensing optical system 33 side and the NBR light emitted from the LED 31c is reflected toward the condensing optical system 33 side.

The LED drive portion 32 is configured to be capable of supplying a drive current for driving each LED provided in the LED light source portion 31. Furthermore, the LED drive portion 32 is configured to be capable of changing the magnitude of the drive current supplied from the LED drive portion 32 to the LED light source portion 31 based on a light adjustment signal outputted from the processor 4 to thereby change the intensity (light quantity) of the light (WB light, NBX light and NBR light) emitted from each LED of the LED light source portion 31. Moreover, the LED drive portion 32 is configured to be capable of causing each LED provided in the LED light source portion 31 to turn on or off based on the light adjustment signal outputted from the processor 4.

The processor 4 includes a pre-processing portion 41, an A/D conversion portion 42, an image processing portion 43, a D/A conversion portion 44, a light adjustment portion 45, a mode switching control portion 46, an image pickup device drive portion 47, and a filter switching control portion 48.

The pre-processing portion 41 is configured to perform processing such as signal amplification and noise removal with respect to an image pickup signal outputted from the scope 2, and to output the image pickup signal that underwent the aforementioned processing to the A/D conversion portion 42 and the light adjustment portion 45.

The A/D conversion portion 42 is configured to convert an analog image pickup signal outputted from the pre-processing portion 41 to digital image data and output the digital image data to the image processing portion 43.

The image processing portion 43 is configured to include functions that can execute processing such as gamma correction and edge enhancement with respect to the image data outputted from the A/D conversion portion 42.

Furthermore, the image processing portion 43 is configured to include a spectral distribution correction portion 43a and a matrix calculation portion 43b.

The spectral distribution correction portion 43a that has a function as a correction processing portion acquires a matrix C having a spectral distribution correction function by performing processing which is described later based on predetermined information outputted from the storage portion 26 accompanying connection of the scope 2 and the processor 4.

The matrix calculation portion 43b that has a function as an image separation processing portion performs processing which is described later based on predetermined information outputted from the storage portion 26 accompanying connection of the scope 2 and the processor 4, and the matrix C acquired by the spectral distribution correction portion 43a to thereby perform calculation processing for acquiring a matrix MAUA having both a spectral distribution correction function and an image separation function. Furthermore, the matrix calculation portion 43b performs calculations by applying the matrix MAUA to image data that is inputted to the image processing portion 43 in the fluorescence observation mode, and also performs processing to allocate the image data of each wavelength band component obtained as a result of the calculations to an R channel, a G channel, and a B channel of the display apparatus 5. The processing performed by the matrix calculation portion 43b will be described in detail later.

Upon detecting that the endoscope apparatus 1 has been switched to the fluorescence observation mode based on the mode switching signal outputted from the mode switching control portion 46, the image processing portion 43 performs processing such as gamma correction and edge enhancement on the image data allocated to the respective color channels of R, G, and B of the display apparatus 5 through the processing by the matrix calculation portion 43b and outputs the image data to the D/A conversion portion 44.

On the other hand, upon detecting that the endoscope apparatus 1 has been switched to the white light observation mode based on the mode switching signal outputted from the mode switching control portion 46, the image processing portion 43 allocates the respective color components included in the image data outputted from the A/D conversion portion 42 to the respective color channels of R, G, and B of the display apparatus 5, further performs processing such as gamma correction and edge enhancement on the image data allocated to the respective color channels, and outputs the image data to the D/A conversion portion 44. That is, according to the present embodiment, the image processing portion 43 is configured so that the calculation processing (by the matrix calculation portion 43b) using the matrix MAUA is not performed when the endoscope apparatus 1 is switched to the white light observation mode.

The D/A conversion portion 44 is configured to convert the image data outputted from the image processing portion 43 to an analog video signal and output the analog video signal to the display apparatus 5.

The light adjustment portion 45 is configured to output a light adjustment signal corresponding to the brightness of the image pickup signal that is outputted from the pre-processing portion 41. More specifically, upon detecting that the endoscope apparatus 1 has been switched to the white light observation mode based on the mode switching signal outputted from the mode switching control portion 46 and the image pickup signal outputted from the pre-processing portion 41, the light adjustment portion 45 outputs to the LED drive portion 32 a light adjustment signal for turning off the LED 31b and the LED 31c and for also causing the LED 31a to emit light at an intensity appropriate for observation in the white light observation mode. Further, upon detecting that the endoscope apparatus 1 has been switched to the fluorescence observation mode based on the mode switching signal outputted from the mode switching control portion 46 and the image pickup signal outputted from the pre-processing portion 41, the light adjustment portion 45 outputs to the LED drive portion 32 a light adjustment signal for turning off the LED 31a and for also causing the LED 31b and the LED 31c to simultaneously emit light at an intensity appropriate for observation in the fluorescence observation mode.

Upon detecting that an instruction for switching the observation mode of the endoscope apparatus 1 to the white light observation mode has been issued at the mode switching switch 25, the mode switching control portion 46 outputs a mode switching signal to the image processing portion 43, the light adjustment portion 45, the image pickup device drive portion 47, and the filter switching control portion 48 so as to perform operations corresponding to the white light observation mode. Further, upon detecting that an instruction for switching the observation mode of the endoscope apparatus 1 to the fluorescence observation mode has been issued at the mode switching switch 25, the mode switching control portion 46 outputs a mode switching signal to the image processing portion 43, the light adjustment portion 45, the image pickup device drive portion 47 and the filter switching control portion 48 so as to perform operations corresponding to the fluorescence observation mode.

Based on the mode switching signal outputted from the mode switching control portion 46, the image pickup device drive portion 47 outputs an image pickup device drive signal to the image pickup device 23 so as to perform an image pickup operation at a timing corresponding to the observation mode that is currently selected and generate an image pickup signal using a gain corresponding to the observation mode that is currently selected.

Upon detecting that the endoscope apparatus 1 has been switched to the white light observation mode based on the mode switching signal outputted from the mode switching control portion 46, the filter switching control portion 48 outputs a filter switching signal to the filter switching apparatus 24 to cause the filter switching apparatus 24 to operate such that the excitation light cut filter 24a retracts from the optical path between the objective optical system 22 and the color filter 23a. Further, upon detecting that the endoscope apparatus 1 has been switched to the fluorescence observation mode based on the mode switching signal outputted from the mode switching control portion 46, the filter switching control portion 48 outputs a filter switching signal to the filter switching apparatus 24 to cause the filter switching apparatus 24 to operate such that the excitation light cut filter 24a is interposed into the optical path between the objective optical system 22 and the color filter 23a.

Next, operations of the endoscope apparatus 1 of the present embodiment will be described.

A user such as a surgeon connects the respective components of the endoscope apparatus 1 and, after turning on the power of the respective components of the endoscope apparatus 1, operates the mode switching switch 25 to set the observation mode of the endoscope apparatus 1 to the white light observation mode.

Upon detecting that an instruction to switch the observation mode of the endoscope apparatus 1 to the white light observation mode was issued at the mode switching switch 25, the mode switching control portion 46 outputs a mode switching signal for performing operations corresponding to the white light observation mode to the image processing portion 43, the light adjustment portion 45, the image pickup device drive portion 47, and the filter switching control portion 48.

Based on the light adjustment signal outputted from the light adjustment portion 45, the LED drive portion 32 turns off the LED 31b and LED 31c of the LED light source portion 31, and causes the LED 31a to emit light at an intensity appropriate for observation in the white light observation mode.

Through such operation of the LED drive portion 32, in the white light observation mode, WB light (white light) as illuminating light supplied from the light source apparatus 3 is emitted to an object via the light guide 7 and the illumination optical system 21, and reflected light of the WB light emitted to the object is impinged on the objective optical system 22 as return light from a site to be observed 101.

The filter switching apparatus 24 operates so as to retract the excitation light cut filter 24a from the optical path between the objective optical system 22 and the color filter 23a based on the filter switching signal outputted from the filter switching control portion 48.

Therefore, in the white light observation mode, the WB light that is incident on the color filter 23a is separated into three color components of R light, G light, and B light, and the light of the three color components into which the WB light was separated is received on the image pickup surface of the image pickup device 23 and, furthermore, an image pickup signal obtained by picking up an image of the light of the three color components that was received is outputted from the image pickup device 23.

The pre-processing portion 41 performs processing such as signal amplification and noise removal with respect to the image pickup signal outputted from the scope 2, and outputs the resulting image pickup signal that underwent the processing to the A/D conversion portion 42.

The A/D conversion portion 42 converts an analog image pickup signal outputted from the pre-processing portion 41 to digital image data, and outputs the digital image data to the image processing portion 43. Through such processing of the A/D conversion portion 42, image data is generated which includes a red color component RC, a green color component GC, and a blue color component BC corresponding to the intensity of the R light, the G light, and the B light received on the image pickup surface of the image pickup device 23.

Upon detecting that the endoscope apparatus 1 has been switched to the white light observation mode based on the mode switching signal outputted from the mode switching control portion 46, the image processing portion 43 allocates the RC, GC, and BC color components included in the image data outputted from the A/D conversion portion 42 to the R, G, and B color channels of the display apparatus 5, respectively, and further performs processing such as gamma correction and edge enhancement on the image data allocated to the respective color channels and outputs the image data to the D/A conversion portion 44.

The display apparatus 5 displays the image of the object corresponding to the video signal outputted via the D/A conversion portion 44.

That is, by performing the operations and the like described above in the white light observation mode, an observed image (color image) corresponding to the white light observation mode is displayed on the display apparatus 5.

On the other hand, before starting observation of the site to be observed 101 in the fluorescence observation mode, the user administers a fluorescent probe (a fluorescent substance) that accumulates in diseased tissue, such as cancer, to the subject (the site to be observed 101). Note that it is assumed that an excitation wavelength of the fluorescent probe (fluorescent substance) according to the present embodiment is included in the wavelength band of the NBX light. Further, it is assumed that when the fluorescent probe (fluorescent substance) is excited by the NBX light in the present embodiment, fluorescence in a wavelength band that does not overlap with the NBR light is emitted.

The user performs an operation to insert the scope 2 while observing the observed image in the white light observation mode that is displayed on the display apparatus 5, and thereby places the distal end portion of the scope 2 in the vicinity of the desired site to be observed 101 inside the subject. In that state, the user or the like operates the mode switching switch 25 to issue an instruction for switching the observation mode of the endoscope apparatus 1 to the fluorescence observation mode.

Upon detecting that an instruction for switching the observation mode of the endoscope apparatus 1 to the fluorescence observation mode was issued at the mode switching switch 25, the mode switching control portion 46 outputs a mode switching signal for causing operations corresponding to the fluorescence observation mode to be performed to the image processing portion 43, the light adjustment portion 45, the image pickup device drive portion 47, and the filter switching control portion 48.

Based on a light adjustment signal outputted from the light adjustment portion 45, the LED drive portion 32 turns off the LED 31*a* of the LED light source portion 31 and also causes the LED 31*b* and the LED 31*c* to simultaneously emit light at an intensity appropriate for observation in the fluorescence observation mode.

As a result of such operations of the LED drive portion 32, in the fluorescence observation mode, NBX light and NBR light supplied from the light source apparatus 3 are emitted to the site to be observed 101 via the light guide 7 and the illumination optical system 21. At such time, the NBX light emitted from the illumination optical system 21 acts as excitation light, and the NBR light emitted from the illumination optical system 21 acts as reference light, and consequently mixed light of FL light as fluorescence and REF light that is reflected light of the NBR light is impinged on the objective optical system 22 as return light from the site to be observed 101.

On the other hand, the filter switching apparatus 24 operates so as to interpose the excitation light cut filter 24*a* into the optical path between the objective optical system 22 and the color filter 23*a* based on the filter switching signal outputted from the filter switching control portion 48.

As a result of such operations of the filter switching apparatus 24, in the fluorescence observation mode, light that has passed through the excitation light cut filter 24*a* and the R filter of the color filter 23*a*, light that has passed through the excitation light cut filter 24*a* and the G filter of the color filter 23*a*, and light that has passed through the excitation light cut filter 24*a* and the B filter of the color filter 23*a* are received on the image pickup surface of the image pickup device 23, and furthermore, an image pickup signal obtained by picking up an image of the respective lights that were received is outputted from the image pickup device 23.

That is, the image pickup device 23 and the color filter 23*a* function as an image pickup portion that, with respect to return light that includes a plurality of wavelength band components generated accompanying irradiation of illuminating light onto the site to be observed 101, receives the return light with different spectral sensitivities for the respective color components to thereby pick up an image of the return light.

The pre-processing portion 41 performs processing such as signal amplification and noise removal with respect to the image pickup signal outputted from the scope 2, and outputs the resulting image pickup signal that underwent the processing to the A/D conversion portion 42.

The A/D conversion portion 42 converts an analog image pickup signal outputted from the pre-processing portion 41 to digital image data, and outputs the digital image data to the image processing portion 43. Through such processing of the A/D conversion portion 42, image data is generated which includes a red color component RD, a green color component GD, and a blue color component BD corresponding to the intensity of the FL light and the REF light received on the image pickup surface of the image pickup device 23.

Upon detecting that the endoscope apparatus 1 has been switched to the fluorescence observation mode based on the mode switching signal outputted from the mode switching control portion 46, the image processing portion 43 operates so as to cause the matrix calculation portion 43*b* to execute calculation processing using the matrix MAUA.

Here, a specific example of processing relating to acquisition of the matrix MAUA that has both a spectral distribution correction function and an image separation function will be described. Note that it is assumed that the processing described hereunder as a specific example of processing relating to acquisition of the matrix MAUA is executed at an arbitrary timing before the observation mode of the endoscope apparatus 1 is switched to the fluorescence observation mode.

Upon detecting that the scope 2 and the processor 4 have been connected, as predetermined information to be used in the calculation processing for acquiring the matrix MAUA, the storage portion 26, for example, outputs information showing the spectral sensitivity characteristics of the respective filters (R filter, G filter, and B filter) of the color filter 23*a* and information showing the spectral distribution of the FL light and REF light that are the return light emitted from the object in the fluorescence observation mode to the image processing portion 43 of the processor 4.

Based on the information showing the spectral sensitivity characteristics of the image pickup device 23 that includes the respective filters (R filter, G filter, and B filter) of the color filter 23*a* and the information showing the spectral distributions of the FL light and REF light emitted from the object in the fluorescence observation mode, the spectral distribution correction portion 43*a* acquires spectral distributions of the red color component RD, the green color component GD, and the blue color component BD that are included in image data inputted into the image processing portion 43 in the fluorescence observation mode.

Further, the spectral distribution correction portion 43*a* normalizes, by a predetermined method, the spectral distributions of the red color component RD, the green color component GD, and the blue color component BD acquired as described above.

Figure 3:
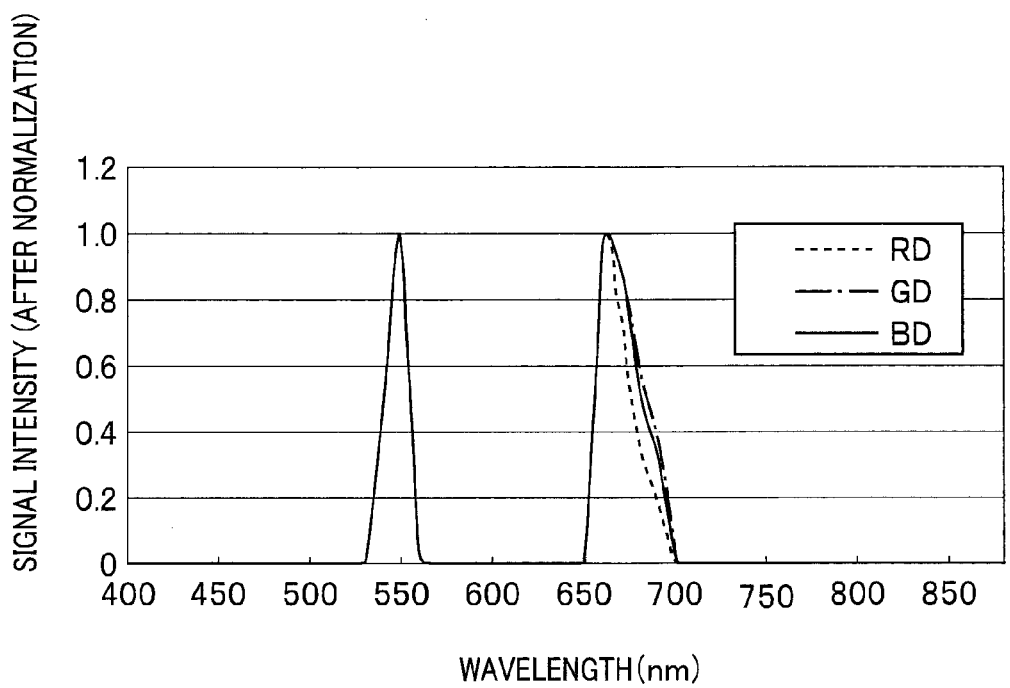
FIG. 3 is a view illustrating an example of normalized spectral distributions of a red color component RD, a green color component GD, and a blue color component BD.

More specifically, for example, in a case in which light in a green region having a peak wavelength in the vicinity of 550 nm is emitted as the REF light, light in a red region having a peak wavelength in the vicinity of 660 nm is emitted as the FL light, and furthermore, normalization is performed by a method that makes the peak values of signal intensities at the peak wavelength of the REF light and the peak wavelength of the FL light 1.0, respectively, the respective spectral distributions of the red color component RD, the green color component GD, and the blue color component BD are normalized as shown in FIG. 3. FIG. 3 is a view that illustrates an example of the normalized spectral distributions of the red color component RD, the green color component GD and the blue color component BD.

According to FIG. 3, spectral distributions obtained in accordance with the signals for each of the color components are mutually different in the band of the FL light having the peak wavelength in the vicinity of 660 nm. This difference in the spectral distributions between the respective color components arises due to the fact that, in the wavelength band of the FL light, the spectral sensitivities for the respective color components of the image pickup device 23 (each filter of the color filter 23a) have respectively different wavelength distributions. Accordingly, in order to favorably perform image separation by means of the matrix calculation portion 43b, it is necessary to previously correct the differences in the spectral distributions among the respective color components as illustrated in FIG. 3 before executing the processing relating to image separation.

Therefore, the spectral distribution correction portion 43a acquires a matrix C of 3 rows and 3 columns in which the respective coefficients are set so as to make the shapes of the normalized spectral distributions match each other.

Figure 4:
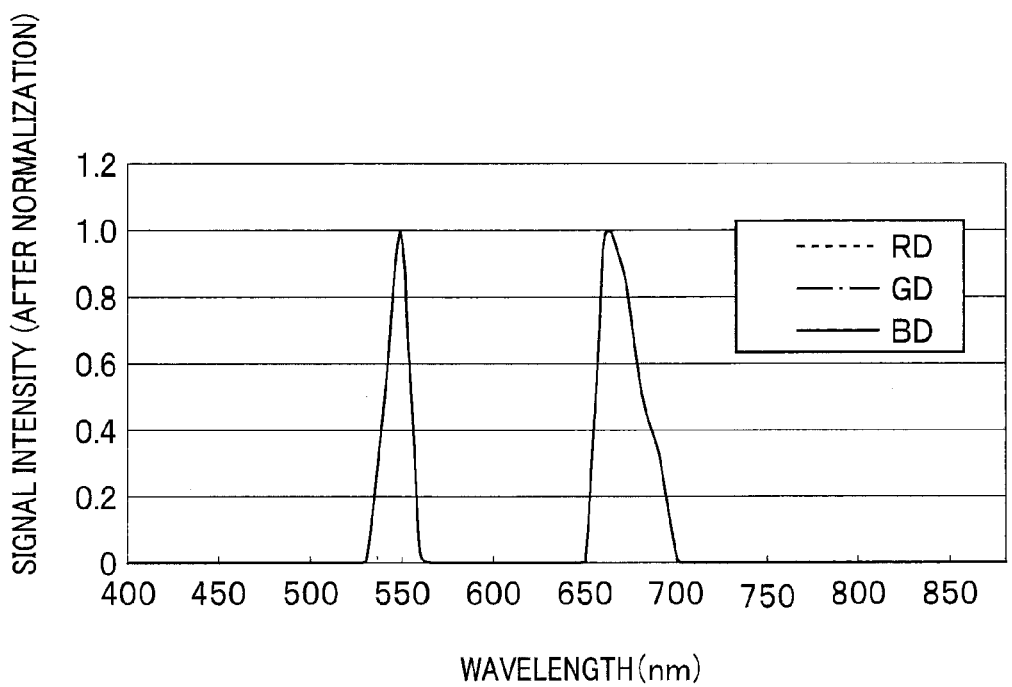
FIG. 4 is a view illustrating an example of a case in which the shapes of the spectral distributions of the red color component RD and the green color component GD in FIG. 3 are caused to match the shape of the spectral distribution of the blue color component BD.

More specifically, the spectral distribution correction portion 43a acquires the matrix C of 3 rows and 3 columns in which, for example, the respective coefficients are set so that the shapes of the spectral distributions of the respective color components shown in FIG. 3 become the shapes shown in FIG. 4. FIG. 4 is a view that illustrates an example of a case where the shapes of the spectral distributions of the red color component RD and the green color component GD in FIG. 3 are caused to match the shape of the spectral distribution of the blue color component BD.

Note that, the spectral distribution correction portion 43a may acquire the matrix C in which the respective coefficients are set so that, with respect to the shape of a spectral distribution of an arbitrary single color component selected from among the red color component RD, the green color component GD, and the blue color component BD, the coefficients cause the shapes of the spectral distributions of the other two color components to match the selected spectral distribution shape, or may acquire the matrix C in which the respective coefficients are set so as to cause the shapes of the spectral distributions of the red color component RD, the green color component GD, and the blue color component BD to each match a predetermined shape.

The matrix C acquired through the processing of the spectral distribution correction portion 43a that is described above has a spectral distribution correction function that is capable of correcting the spectral distributions of the respective color components (red color component RD, green color component GD, and blue color component BD) before normalization, that is, correcting the shapes of the spectral distributions of the respective color components (red color component RD, green color component GD, and blue color component BD) of image data generated based on the FL light and the REF light received on the image pickup surface of the image pickup device 23 when operating in the fluorescence observation mode so as to become similar shapes to each other.

On the other hand, the matrix calculation portion 43b acquires a matrix MAUA by performing the following processing and the like based on the matrix C of 3 rows and 3 columns acquired by the processing of the spectral distribution correction portion 43a as described above, information showing the spectral sensitivity characteristics of the respective filters (R filter, G filter, and B filter) of the color filter 23a, and information showing the spectral distributions of the FL light and REF light emitted from the object in the fluorescence observation mode.

First, based on the information showing the spectral sensitivity characteristics of the respective filters (R filter, G filter, and B filter) of the color filter 23a, and the information showing the spectral distributions of the FL light and REF light emitted from the object in the fluorescence observation mode, the matrix calculation portion 43b defines a matrix corresponding to the intensity of the red color component RD, the green color component GD, and the blue color component BD included in image data $I_{RGB}$ that is inputted to the image processing portion 43 in the fluorescence observation mode, as shown in the following equation (1). Note that, in the following equation (1), it is assumed that $R_{FL}$ represents the intensity of the red color component based on the wavelength component of the FL light received via the R filter of the color filter 23a, $G_{FL}$ represents the intensity of the green color component based on the wavelength component of the FL light received via the G filter of the color filter 23a, $B_{FL}$ represents the intensity of the blue color component based on the wavelength component of the FL light received via the B filter of the color filter 23a, $R_{REF}$ represents the intensity of the red color component based on the wavelength component of the REF light received via the R filter of the color filter 23a, $G_{REF}$ represents the intensity of the green color component based on the wavelength component of the REF light received via the G filter of the color filter 23a, and $B_{REF}$ represents the intensity of the blue color component based on the wavelength component of the REF light received via the B filter of the color filter 23a.

$$I_{RGB} = \begin{pmatrix} R_{FL} & R_{REF} \\ G_{FL} & G_{REF} \\ B_{FL} & B_{REF} \end{pmatrix} \quad (1)$$

Here, when a matrix for separating image data of two mutually independent color components from the respective color components included in the image data inputted to the image processing portion 43 in the fluorescence observation mode is set as MAU, and a matrix representing the image data of the two color components after separation is set as S, the relations shown in the following equations (2) and (3) are established.

$$S = MAU \cdot C \cdot I_{RGB} \quad (2)$$

$$S = \begin{pmatrix} 1 & 0 \\ 0 & 1 \end{pmatrix} \quad (3)$$

Further, the matrix calculation portion 43b determines the matrix MAU of 2 rows and 3 columns by performing the calculation in the following equation (4) based on the above described equations (2) and (3). Note that it is assumed that $(C \cdot I_{RGB})^+$ in the following equation (4) represents a pseudo-inverse matrix of the product of the matrix C of 3 rows and 3 columns and a matrix $I_{RGB}$ of 3 rows and 2 columns as represented by the above described equation (1).

$$MAU = S \cdot (C \cdot I_{RGB})^+ = \begin{pmatrix} M11 & M12 & M13 \\ M21 & M22 & M23 \end{pmatrix} \quad (4)$$

According to the processing using the matrix MAU determined through the calculation of equation (4) above, it is possible to separate image data including only a red color component FLRD based on the wavelength component of the FL light from the respective color components included in the image data inputted to the image processing portion 43 in the fluorescence observation mode.

Further, according to the processing using the matrix MAU determined through the calculation of equation (4) above, it is possible to separate image data including only a green color component REFGD based on the wavelength component of the REF light from the respective color components included in the image data inputted to the image processing portion 43 in the fluorescence observation mode.

According to the processing using the matrix MAU determined through the calculation of equation (4) above, image data of the aforementioned red color component FLRD and green color component REFGD can be obtained, respectively, whereas image data of the blue color component cannot be obtained. Therefore, the matrix calculation portion 43b of the present embodiment acquires a matrix MAUA of 3 rows and 3 columns expressed as the following equation (5) whose coefficients are set so as to enable the obtainment of image data of a blue color component REFBD having the same intensity as that of the image data of the aforementioned green color component REFGD. Note that coefficients M11, M12, M13, M21, M22 and M23 in the following equation (5) are assumed to have the same values as the respective coefficients included in the matrix MAU of 2 rows and 3 columns determined through the calculation of equation (4) above.

$$MAUA = \begin{pmatrix} M11 & M12 & M13 \\ M21 & M22 & M23 \\ M21 & M22 & M23 \end{pmatrix} \quad (5)$$

That is, the matrix calculation portion 43b acquires a matrix MAUA expressed as the above equation (5) by performing the processing and the like that is described above based on the matrix C of 3 rows and 3 columns, information showing the spectral sensitivity characteristics of the respective filters (R filter, G filter, and B filter) of the color filter 23a, and information showing the spectral distributions of the FL light and REF light emitted from the object in the fluorescence observation mode.

The matrix calculation portion 43b then performs calculations by applying the previously acquired matrix MAUA to the red color component RD, the green color component GD, and the blue color component BD included in the image data inputted to the image processing portion 43 in the fluorescence observation mode, and thereby acquires image data of the red color component FLRD having the intensity corresponding to coefficients M11, M12 and M13, image data of the green color component REFGD having the intensity corresponding to coefficients M21, M22 and M23, and image data of the blue color component REFBD having the intensity corresponding to coefficients M21, M22 and M23, that are expressed as the following equation (6).

$$\begin{pmatrix} FLRD \\ REFGD \\ REFBD \end{pmatrix} = \begin{pmatrix} M11 \cdot RD + M12 \cdot GD + M13 \cdot BD \\ M21 \cdot RD + M22 \cdot GD + M23 \cdot BD \\ M21 \cdot RD + M22 \cdot GD + M23 \cdot BD \end{pmatrix} \quad (6)$$

Furthermore, the matrix calculation portion 43b allocates the image data of the red color component FLRD to the R channel of the display apparatus 5, allocates the image data of the green color component REFGD to the G channel of the display apparatus 5, and allocates the image data of the blue color component REFBD to the B channel of the display apparatus 5.

Thereafter, the image processing portion 43 executes processing such as gamma correction and edge enhancement on the image data allocated to the respective color channels of R, G, and B of the display apparatus 5 through the processing of the matrix calculation portion 43b, and outputs the image data to the D/A conversion portion 44.

The display apparatus 5 then displays an image of the object corresponding to the video signal outputted via the D/A conversion portion 44.

That is, as a result of performing the above-described operations and the like in the fluorescence observation mode, an observed image (pseudo-color image) corresponding to the fluorescence observation mode is displayed on the display apparatus 5.

The R filter, the G filter and the B filter of the color filter 23a have transmission characteristics over a wide band from a visible region to a near-infrared region, respectively. For this reason, the component based on the wavelength component of the FL light received via the R filter of the color filter 23a and the component based on the wavelength component of the REF light received via the R filter of the color filter 23a are mixed with the red color component RD that is inputted to the image processing portion 43 when operating in the fluorescence observation mode of the present embodiment. Furthermore, the component based on the wavelength component of the FL light received via the G filter of the color filter 23a and the component based on the wavelength component of the REF light received via the G filter of the color filter 23a are mixed with the green color component GD included in the image data that is inputted to the image processing portion 43 when operating in the fluorescence observation mode of the present embodiment. Therefore, if the red color component RD is allocated as it is to the R channel of the display apparatus 5 and the green color component GD is allocated as it is to the G channel of the display apparatus 5, a problem will arise that an observed image is not displayed with an originally intended color tone.

According to the present embodiment, to solve the aforementioned problem, before allocating the color components to the R, G, and B channels of the display apparatus 5, processing using the matrix MAUA having an image separation function is performed by the matrix calculation portion 43b to thereby enable the obtainment of image data of the red color component FLRD and of the green color component REFGD, respectively, that is mutually independent image data for the respective wavelength band components.

Further, according to the present embodiment, by providing the matrix MAUA with both a spectral distribution correction function and an image separation function, the image data of the red color component FLRD and the green color component REFGD can be obtained as image data that is mutually independent image data for the respective wavelength band components, and in which color mixing that arises due to a combination of the spectral sensitivity characteristics of the respective filters (R filter, G filter, and B filter) included in the color filter 23a and the wavelength bands of the return light (FL light and REF light) impinged on the color filter 23a is eliminated.

Figure 5:
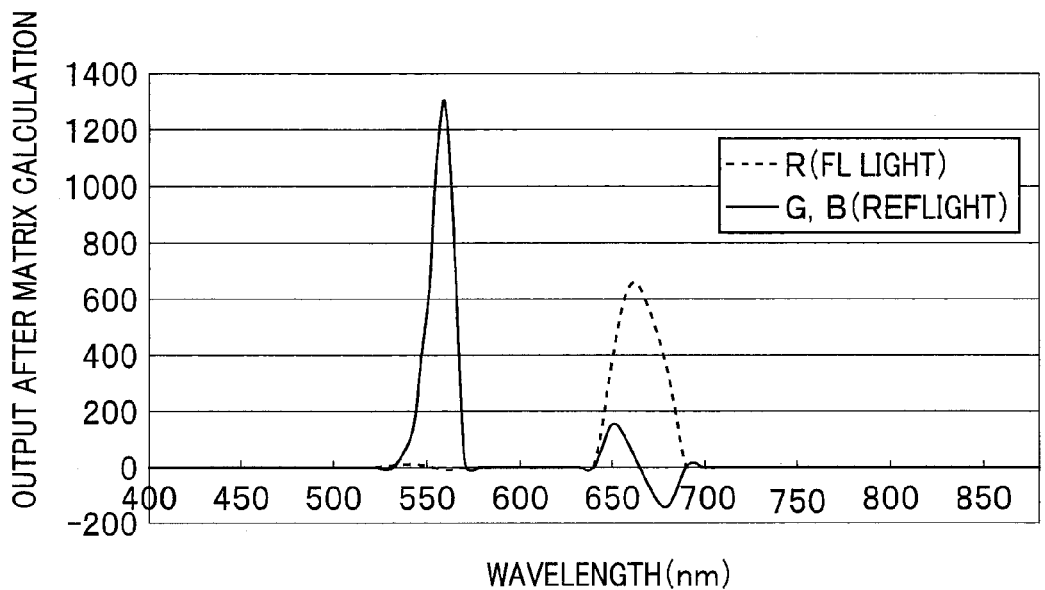
FIG. 5 is a view illustrating an example of spectral distributions obtained as a calculation result when a calculation relating to image separation is performed using a matrix that does not have a spectral distribution correction function.

In this connection, to include a spectral distribution correction function in the matrix MAUA, the matrix C included in each of the above described equation (2) and equation (4) is set, for example, as a matrix having respective coefficients such that the spectral distributions between signals of the respective color components are caused to match. In contrast, for example, in a case where it is assumed that the matrix C is a unit matrix, that is, when it is assumed that the matrix MAUA does not substantially have a spectral distribution correction function, output values of the signals of the respective color components having the spectral distributions shown in FIG. 5 are obtained when a calculation is performed using the matrix MAUA. FIG. 5 is a view that illustrates an example of spectral distributions obtained as a calculation result when a calculation relating to image separation was performed using a matrix that does not have a spectral distribution correction function.

According to the spectral distribution of the R component shown in FIG. 5, an output value of another wavelength band component other than a wavelength band component corresponding to FL light as light of the red region having a peak wavelength in the vicinity of 660 nm fluctuates little from the vicinity of 0, that is, the wavelength component of the FL light is appropriately separated.

Further, according to the spectral distribution of the G component (B component) in FIG. 5, apart from a wavelength band component corresponding to the REF light as light of the green region having a peak wavelength in the vicinity of 550 nm, a clear fluctuation in the output value also arises in a wavelength band component corresponding to the FL light, that is, it is found that a wavelength component of the REF light is not appropriately separated.

Figure 6:
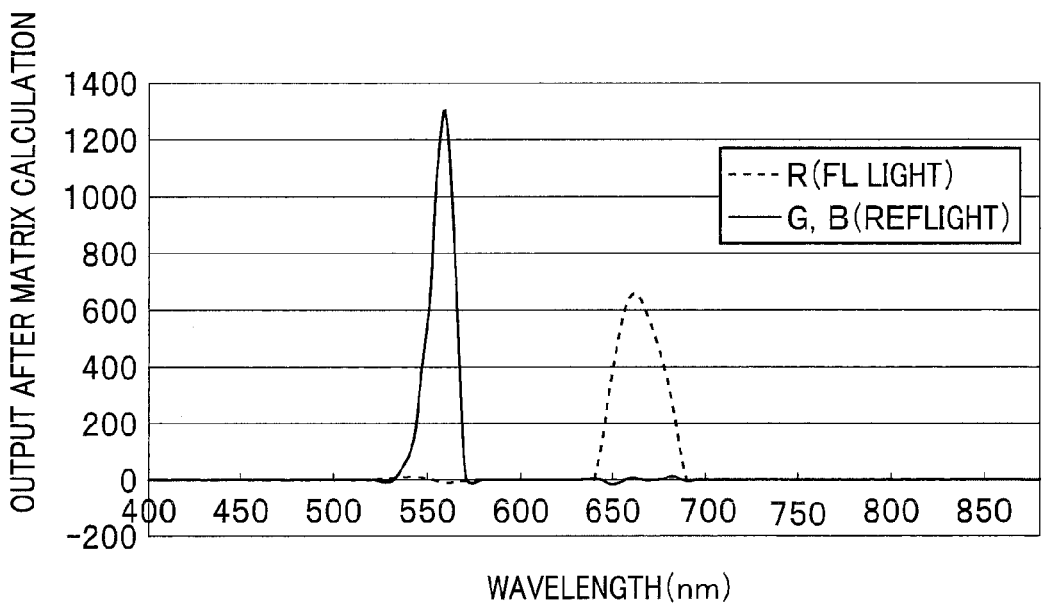
FIG. 6 is a view illustrating an example of spectral distributions obtained as a calculation result when a calculation relating to image separation is performed using a matrix having a spectral distribution correction function.

In contrast, according to the present embodiment, by performing a calculation using the matrix MAUA having a spectral distribution correction function, for example, output values of signals of respective color components having the spectral distributions shown in FIG. 6 are obtained. FIG. 6 is a view illustrating an example of spectral distributions obtained as a calculation result when a calculation relating to image separation is performed using a matrix having a spectral distribution correction function.

According to the spectral distribution of the R component shown in FIG. 6, an output value of another wavelength band component other than a wavelength band component corresponding to FL light as light of the red region having a peak wavelength in the vicinity of 660 nm fluctuates little from the vicinity of 0, that is, the wavelength component of the FL light is appropriately separated.

Further, according to the spectral distribution of the G component (B component) in FIG. 6, a clear fluctuation in an output value does not arise in another wavelength band component (wavelength band component corresponding to FL light) other than a wavelength band component corresponding to the REF light as light of the green region having a peak wavelength in the vicinity of 550 nm, that is, it is found that a wavelength component of the REF light is also appropriately separated.

Therefore, according to the present embodiment, an image including a plurality of color components obtained by a simultaneous image pickup method can be favorably separated into images for respective wavelength band components that are mutually independent.

Note that the endoscope apparatus 1 according to the present embodiment is not limited to an endoscope apparatus having a configuration such that, upon the scope 2 and the processor 4 being connected, information showing the spectral sensitivity characteristics of each filter (R filter, G filter, and B filter) of the color filter 23a and information showing the spectral distributions of FL light and REF light as return light emitted from an object in the fluorescence observation mode are outputted from the storage portion 26, and processing relating to acquisition of the matrix C is then performed based on the respective information that was outputted and the like.

More specifically, the endoscope apparatus 1 according to the present embodiment, for example, may have a configuration such that image pickup device identification information that can identify the kind of the image pickup device 23 (and color filter 23a) provided in the scope 2 and fluorescent probe identification information that can identify the kind of fluorescent probes that corresponds to the observation (is compatible with the transmission wavelength band of the excitation light cut filter 24a) by the scope 2 are stored beforehand in the storage portion 26, and a plurality of matrices C that are calculated in advance in accordance with combinations of different kinds of image pickup devices and different kinds of fluorescent probes are stored in the spectral distribution correction portion 43a. According to this configuration, the spectral distribution correction portion 43a can quickly and easily acquire one matrix C to be used in processing relating to acquisition of the matrix MAUA from among the previously calculated plurality of matrices C based on image pickup device identification information and fluorescent probe identification information outputted from the storage portion 26 upon the scope 2 and the processor 4 being connected.

Note that, according to the present embodiment, a configuration may also be adopted in which information relating to a fluorescent probe (for example, a name or an identification code of a fluorescence agent) to be used in the fluorescence observation mode is inputted by operating the input apparatus 6, and the matrix C is set (by the spectral distribution correction portion 43a) in accordance with the inputted information relating to the fluorescent probe.

Further, according to the present embodiment, a configuration may also be adopted in which the respective coefficients of the matrix MAUA can be changed to an arbitrary value in accordance with an input operation performed at the input apparatus 6.

Furthermore, according to the present embodiment, for example, in a case in which the scope 2 is configured to be capable of picking up fluorescence images of a plurality of fluorescent probes that have substantially the same excitation wavelength as each other that is included in a wavelength band of NBX light and that have mutually different fluorescence wavelengths, a configuration may also be adopted so that information of a single fluorescent probe selected from among the plurality of fluorescent probes can be inputted by an operation at the input apparatus 6, and furthermore, so that a single matrix C to be used in processing relating to acquisition of the matrix MAUA is acquired (selected) (by the spectral distribution correction portion 43a) from among a plurality of matrices C that were previously calculated, based on the inputted fluorescent probe information and the aforementioned image pickup device identification information.

Further, the matrix MAUA acquired through the aforementioned processing is suitable for a case of performing observation after administering a fluorescent probe having a fluorescence wavelength in a range from the red region to the near-infrared region, such as Cy5, Cy5.5, Cy7, ICG, and IR-Dye800, to the site to be observed 101. However, for example, by appropriately changing a part of the processing relating to acquisition of the matrix MAUA, it is also possible to acquire a matrix MAUA suitable for a case of performing observation after administering a fluorescent probe having a fluorescence wavelength in the green region, such as fluorescein, to the site to be observed 101. Note that, in such case, taking into consideration the fact that the FL light is light of the green region, it is desirable to set the wavelength band of the REF light to a wavelength band that does not overlap with the FL light, such as, for example, a wavelength band in the red region.

The present embodiment can also be applied, for example, to a case of simultaneously observing fluorescence in the green region that is emitted from fluorescein administered to the site to be observed 101 and fluorescence in the near-infrared region emitted from ICG administered to the site to be observed 101, that is, a case of simultaneously observing the fluorescence emitted from an object to which a plurality of fluorescent probes having different fluorescence wavelengths to each other were administered.

Figure 7:
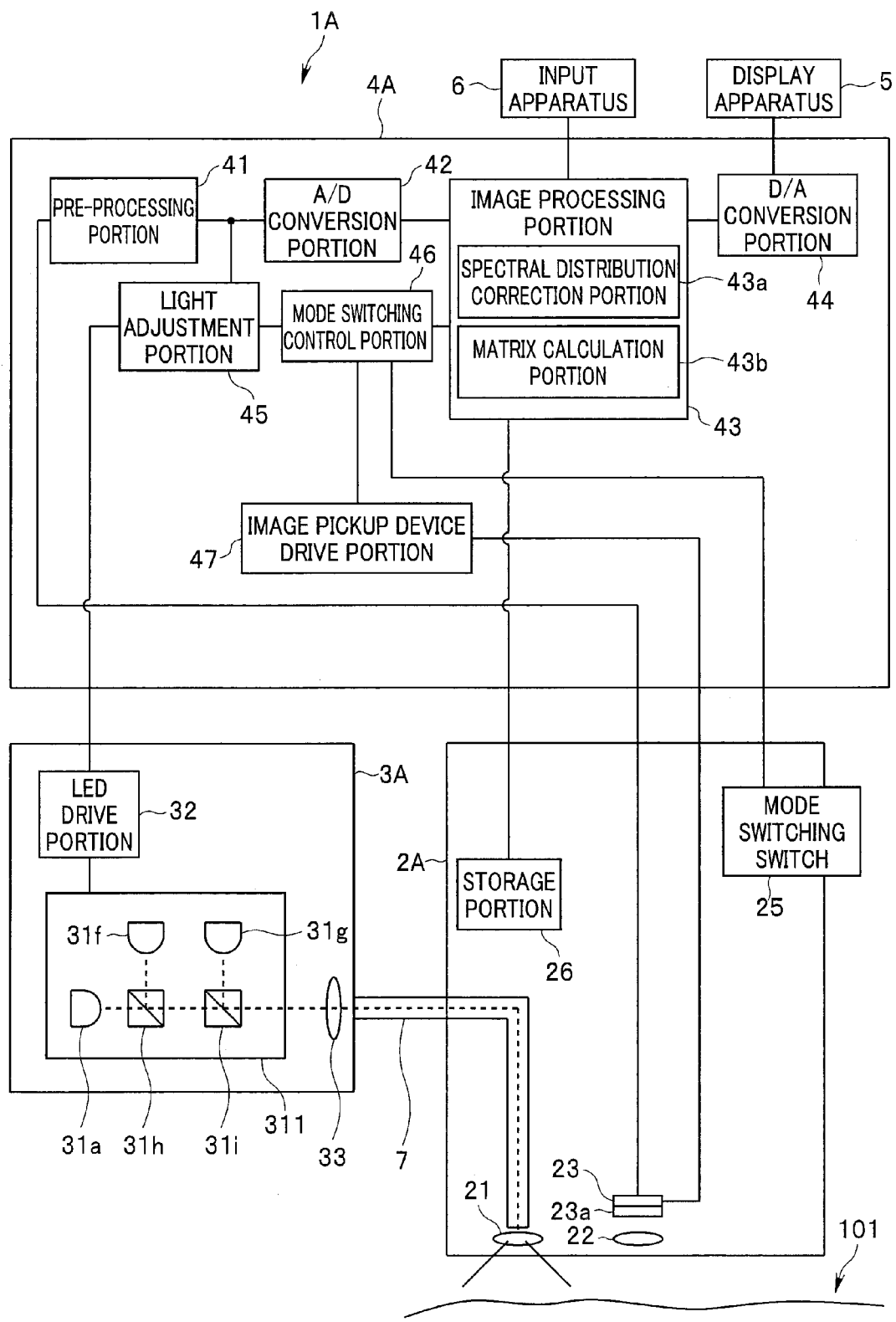
FIG. 7 is a view illustrating a configuration of main components of an endoscope apparatus according to a first modification of the embodiment of the present invention.

The matrix C and matrix MAUA acquired according to the present embodiment are not limited to matrices in which each coefficient is set so as to correspond to FL light and REF light as return light generated in the fluorescence observation mode. For example, in the matrix C and matrix MAUA, each coefficient may also be set to correspond to blue narrow-band light and green narrow-band light as return light (reflected light) generated in a narrow-band light observation mode for observing capillary vessels that are present in a surface layer of biological mucosa and blood vessels present at a deeper position than the surface layer of biological mucosa (hereinafter, also referred to as "intermediate layer"). A specific example of such a case will be described hereunder. FIG. 7 is a view that illustrates a configuration of main components of an endoscope apparatus according to a first modification of the embodiment of the present invention. Note that, in the following description, for brevity, a detailed description relating to portions to which the configuration and the like described already in relation to the endoscope apparatus 1 can be applied is omitted, and the description mainly relates to portions having a different configuration and the like to the endoscope apparatus 1.

As shown in FIG. 7, an endoscope apparatus 1A includes a scope 2A having the same configuration as the scope 2 except that the filter switching apparatus 24 is omitted therefrom, a light source apparatus 3A having the same configuration as the light source apparatus 3 except that an LED light source portion 311 is provided instead of the LED light source portion 31, and a processor 4A having the same configuration as the processor 4 except that the filter switching control portion 48 is omitted therefrom.

The mode switching switch 25 of the scope 2A is configured to be capable of issuing an instruction for switching the observation mode of the endoscope apparatus 1A to any single observation mode selected from the white light observation mode and a narrow-band light observation mode in accordance with an operation by a surgeon or the like.

The LED light source portion 311 is configured to include the LED 31a that emits WB light that is wide-band light, an LED 31f that emits NBG light that is light with which blood vessels present in an intermediate layer in biological mucosa can be observed, an LED 31g that emits NBB light that is light with which capillary vessels present in a surface layer of biological mucosa can be observed, an optical element 31h, and an optical element 31i.

The LED 31f is configured to be capable of emitting narrow band light whose center wavelength is set, for example, to 540 nm as the NBG light.

The LED 31g is configured to be capable of emitting narrow band light whose center wavelength is set, for example, to 415 nm as the NBB light.

The optical element 31h is constituted by, for example, a half mirror, and has optical characteristics such that the WB light emitted from the LED 31a is transmitted to the optical element 31i side and the NBG light emitted from the LED 31f is reflected toward the optical element 31i side.

The optical element 31i is constituted by, for example, a half mirror, and has optical characteristics such that the WB light and NBG light emitted via the optical element 31h are transmitted to the condensing optical system 33 side, and the NBB light emitted from the LED 31g is reflected toward the condensing optical system 33 side.

The spectral distribution correction portion 43a of the processor 4A acquires a matrix Ca having a spectral distribution correction function by performing processing based on pre-determined information outputted from the storage portion 26 accompanying connection of the scope 2A and the processor 4A.

The matrix calculation portion 43b of the processor 4A performs processing based on predetermined information outputted from the storage portion 26 accompanying connection of the scope 2A and the processor 4A and the matrix Ca acquired by the spectral distribution correction portion 43a to thereby perform calculation processing for acquiring a matrix MAUB having both a spectral distribution correction function and an image separation function. Further, the matrix calculation portion 43b of the processor 4A performs calculations by applying the matrix MAUB to image data inputted to the image processing portion 43 in the narrow-band light observation mode, and also performs processing to allocate the image data of each wavelength band component obtained as a result of the calculations to the R channel, G channel, and B channel of the display apparatus 5.

Upon detecting that the endoscope apparatus 1A has been switched to the white light observation mode based on the mode switching signal outputted from the mode switching control portion 46 and the image pickup signal outputted from the pre-processing portion 41, the light adjustment portion 45 of the processor 4A outputs to the LED drive portion 32 a light adjustment signal for turning off the LED 31f and the LED 31g and for also causing the LED 31a to emit light at an intensity appropriate for observation in the white light observation mode. Further, upon detecting that the endoscope apparatus 1A has been switched to the narrow-band light observation mode based on the mode switching signal outputted from the mode switching control portion 46 and the image pickup signal outputted from the pre-processing portion 41, the light adjustment portion 45 of the processor 4A outputs to the LED drive portion 32 a light adjustment signal for turning off the LED 31a and for also causing the LED 31f and the LED 31g to simultaneously emit light at an intensity appropriate for observation in the narrow-band light observation mode.

Upon detecting that an instruction for switching the observation mode of the endoscope apparatus 1A to the white light observation mode has been issued at the mode switching switch 25, the mode switching control portion 46 of the processor 4A outputs a mode switching signal to the image processing portion 43, the light adjustment portion 45, and the image pickup device drive portion 47 so as to perform operations corresponding to the white light observation mode. Further, upon detecting that an instruction for switching the observation mode of the endoscope apparatus 1A to the narrow-band light observation mode has been issued at the mode switching switch 25, the mode switching control portion 46 of the processor 4A outputs a mode switching signal to the image processing portion 43, the light adjustment portion 45, and the image pickup device drive portion 47 so as to perform operations corresponding to the narrow-band light observation mode.

Next, operations of the endoscope apparatus 1A according to the first modification will be described. Note that since operations and the like of the respective portions in a case where the observation mode of the endoscope apparatus 1A is set to the white light observation mode are the same as in the case of the endoscope apparatus 1, a description of those operations is omitted hereunder.

The user performs an operation to insert the scope 2A while observing the observed image in the white light observation mode that is displayed on the display apparatus 5, and thereby places the distal end portion of the scope 2A in the vicinity of the desired site to be observed 101 inside the subject. In that state, the user or the like operates the mode switching switch 25 to issue an instruction for switching the observation mode of the endoscope apparatus 1A to the narrow-band light observation mode.

Upon detecting that an instruction for switching the observation mode of the endoscope apparatus 1A to the narrow-band light observation mode was issued at the mode switching switch 25, the mode switching control portion 46 outputs a mode switching signal for causing operations corresponding to the narrow-band light observation mode to be performed to the image processing portion 43, the light adjustment portion 45, and the image pickup device drive portion 47.

Based on a light adjustment signal outputted from the light adjustment portion 45, the LED drive portion 32 turns off the LED 31a of the LED light source portion 31 and also causes the LED 31f and the LED 31g to simultaneously emit light at an intensity appropriate for observation in the narrow-band light observation mode.

As a result of such operations of the LED drive portion 32, in the narrow-band light observation mode, the NBG light and NBB light supplied from the light source apparatus 3A is emitted to the site to be observed 101 via the light guide 7 and the illumination optical system 21, and mixed light of REG light that is reflected light of the NBG light and REB light that is reflected light of the NBB light is impinged on the objective optical system 22 as return light from the site to be observed 101.

On the other hand, the image pickup device 23 receives light that has passed through the R filter of the color filter 23a, light that has passed through the G filter of the color filter 23a, and light that has passed through the B filter of the color filter 23a, respectively, and generates and outputs an image pickup signal obtained by picking up images of the respective lights that were received.

The pre-processing portion 41 performs processing such as signal amplification and noise removal with respect to the image pickup signal outputted from the scope 2A, and outputs the resulting image pickup signal that underwent the processing to the A/D conversion portion 42.

The A/D conversion portion 42 converts an analog image pickup signal outputted from the pre-processing portion 41 to digital image data and outputs the digital image data to the image processing portion 43. Through such processing of the A/D conversion portion 42, image data is generated which includes a red color component RD 1, a green color component GD 1, and a blue color component BD 1 corresponding to the intensity of the REG light and REB light received at (the image pickup surface of) the image pickup device 23.

Upon detecting that the endoscope apparatus 1A has been switched to the narrow-band light observation mode based on the mode switching signal outputted from the mode switching control portion 46, the image processing portion 43 operates so as to cause the matrix calculation portion 43b to execute calculation processing using the matrix MAUB.

Here, processing relating to acquisition of the matrix MAUB that has both a spectral distribution correction function and an image separation function will be described. Note that it is assumed that the processing relating to acquisition of the matrix MAUB is executed at an arbitrary timing before the observation mode of the endoscope apparatus 1A is switched to the narrow-band light observation mode.

Upon detecting that the scope 2A and the processor 4A have been connected, as predetermined information to be used in the calculation processing for acquiring the matrix MAUB, the storage portion 26, for example, outputs information showing the spectral sensitivity characteristics of the respective filters (R filter, G filter, and B filter) of the color filter 23a and information showing the spectral distribution of the REG light and REB light that are the return light emitted from the object in the narrow-band light observation mode to the image processing portion 43 of the processor 4A.

Based on the information showing the spectral sensitivity characteristics of the image pickup device 23 that includes the respective filters (R filter, G filter, and B filter) of the color filter 23a and the information showing the spectral distributions of the REG light and REB light emitted from the object in the narrow-band light observation mode, the spectral distribution correction portion 43a acquires spectral distributions of the red color component RD1, the green color component GD1, and the blue color component BD1 that are included in image data inputted to the image processing portion 43 in the narrow-band light observation mode.

Further, by the method mentioned previously (method that makes a peak value of a signal intensity for each peak wavelength 1.0, respectively), the spectral distribution correction portion 43a normalizes the spectral distributions of the red color component RD1, the green color component GD1, and the blue color component BD1 acquired as described above. By performing this normalization, differences between the spectral distributions of the respective color components become evident.

Further, the spectral distribution correction portion 43a acquires a matrix Ca of 3 rows and 3 columns in which the respective coefficients are set so as to make the shapes of the normalized spectral distributions match each other.

The matrix Ca acquired through the processing of the spectral distribution correction portion 43a that is described above has a spectral distribution correction function that is capable of correcting the spectral distributions of the respective color components (red color component RD1, green color component GD1, and blue color component BD1) before normalization, that is, correcting the shapes of the spectral distributions of the respective color components (red color component RD1, green color component GD1, and blue color component BD1) of image data generated based on the REG light and the REB light received on the image pickup surface of the image pickup device 23 when operating in the narrow-band light observation mode so as to become similar shapes to each other.

On the other hand, the matrix calculation portion 43b acquires a matrix MAUB by performing the following processing and the like based on the matrix Ca of 3 rows and 3 columns acquired by the processing of the spectral distribution correction portion 43a as described above, information showing the spectral sensitivity characteristics of the respective filters (R filter, G filter, and B filter) of the color filter 23a, and information showing the spectral distributions of the REG light and REB light emitted from the object in the narrow-band light observation mode.

First, based on the information showing the spectral sensitivity characteristics of the respective filters (R filter, G filter, and B filter) of the color filter 23a, and the information showing the spectral distributions of the REG light and REB light emitted from the object in the narrow-band light observation mode, the matrix calculation portion 43b defines a matrix corresponding to the intensity of the red color component RD1, the green color component GD1, and the blue color component BD1 included in image data I'$_{RGB}$ that is inputted to the image processing portion 43 in the narrow-band light observation mode, as shown in the following equation (7). Note that, in the following equation (7), it is assumed that R$_{REB}$ represents the intensity of the red color component based on the wavelength component of the REB light received via the R filter of the color filter 23a, G$_{REB}$ represents the intensity of the green color component based on the wavelength component of the REB light received via the G filter of the color filter 23a, B$_{REB}$ represents the intensity of the blue color component based on the wavelength component of the REB light received via the B filter of the color filter 23a, R$_{REG}$ represents the intensity of the red color component based on the wavelength component of the REG light received via the R filter of the color filter 23a, G$_{REG}$ represents the intensity of the green color component based on the wavelength component of the REG light received via the G filter of the color filter 23a, and B$_{REG}$ represents the intensity of the blue color component based on the wavelength component of the REG light received via the B filter of the color filter 23a.

$$I'_{RGB} = \begin{pmatrix} R_{REB} & R_{REG} \\ G_{REB} & G_{REG} \\ B_{REB} & B_{REG} \end{pmatrix} \quad (7)$$

Here, when a matrix for separating image data of two mutually independent color components from the respective color components included in the image data inputted to the image processing portion 43 in the narrow-band light observation mode is set as MAUb, and a matrix representing the image data of the two color components after separation is set as S, the relations shown in the following equations (8) and (9) are established.

$$S = MAUb \cdot Ca \cdot I'_{RGB} \quad (8)$$

$$S = \begin{pmatrix} 1 & 0 \\ 0 & 1 \end{pmatrix} \quad (9)$$

Further, the matrix calculation portion 43b determines the matrix MAUb of 2 rows and 3 columns by performing the calculation in the following equation (10) based on the above described equations (8) and (9). Note that it is assumed that (Ca·I'$_{RGB}$)$^+$ in the following equation (10) represents a pseudo-inverse matrix of the product of the matrix Ca of 3 rows and 3 columns and a matrix I'$_{RGB}$ of 3 rows and 2 columns as represented by the above described equation (7).

$$MAUb = S \cdot (Ca \cdot I'_{RGB})^+ = \begin{pmatrix} M31 & M32 & M33 \\ M41 & M42 & M43 \end{pmatrix} \quad (10)$$

According to the processing using the matrix MAUb determined through the calculation of equation (10) above, it is possible to separate image data including only a blue color component REBBD based on the wavelength component of the REB light from the respective color components included in the image data inputted to the image processing portion 43 in the narrow-band light observation mode.

Further, according to the processing using the matrix MAUb determined through the calculation of equation (10) above, it is possible to separate image data including only a green color component REGGD based on the wavelength component of the REG light from the respective color components included in the image data inputted to the image processing portion 43 in the narrow-band light observation mode.

According to the processing using the matrix MAUb determined through the calculation of equation (10) above, image data of the aforementioned blue color component REBBD and green color component REGGD can be obtained, respectively, whereas image data of the red color component cannot be obtained. Therefore, the matrix calculation portion 43b of the first modification, for example, acquires a matrix MAUB of 3 rows and 3 columns expressed as the following equation (11) whose coefficients are set so as to enable the obtainment of image data of a red color component RERRD having the same intensity as that of the image data of the aforementioned green color component REGGD. Note that coefficients M31, M32, M33, M41, M42 and M43 in the following equation (11) are assumed to have the same values as the respective coefficients included in the matrix MAUb of 2 rows and 3 columns determined through the calculation of equation (10) above.

$$MAUB = \begin{pmatrix} M31 & M32 & M33 \\ M31 & M32 & M33 \\ M41 & M42 & M43 \end{pmatrix} \quad (11)$$

That is, the matrix calculation portion 43b acquires a matrix MAUB expressed as the above equation (11) by performing the processing and the like described above based on the matrix Ca of 3 rows and 3 columns, information showing the spectral sensitivity characteristics of the respective filters (R filter, G filter, and B filter) of the color filter 23a, and information showing the spectral distributions of the REG light and REB light emitted from the object in the narrow-band light observation mode.

The matrix calculation portion 43b then performs calculations by applying the previously acquired matrix MAUB to the red color component RD1, the green color component GD1, and the blue color component BD1 included in the image data that is inputted to the image processing portion 43 in the narrow-band light observation mode, and thereby acquires image data of the red color component RERRD having the intensity corresponding to coefficients M31, M32 and M33, image data of the green color component REGGD having the intensity corresponding to coefficients M31, M32 and M33, and image data of the blue color component REBBD having the intensity corresponding to coefficients M41, M42 and M43, that are expressed as the following equation (12).

$$\begin{pmatrix} RGRRD \\ REGGD \\ REBBD \end{pmatrix} = \begin{pmatrix} M31 \cdot RD1 + M32 \cdot GD1 + M33 \cdot BD1 \\ M31 \cdot RD + M32 \cdot GD1 + M33 \cdot BD1 \\ M41 \cdot RD + M42 \cdot GD1 + M43 \cdot BD1 \end{pmatrix} \quad (12)$$

Furthermore, the matrix calculation portion 43b allocates the image data of the red color component RERRD to the R channel of the display apparatus 5, allocates the image data of the green color component REGGD to the G channel of the display apparatus 5, and allocates the image data of the blue color component REBBD to the B channel of the display apparatus 5.

Thereafter, the image processing portion 43 executes processing such as gamma correction and edge enhancement with respect to the image data allocated to the respective color channels of R, G and B of the display apparatus 5 through the processing of the matrix calculation portion 43b, and outputs the image data to the D/A conversion portion 44.

The display apparatus 5 then displays an image of the object corresponding to the video signal outputted via the D/A conversion portion 44.

That is, as a result of performing the above-described operations and the like in the narrow-band light observation mode, an observed image corresponding to the narrow-band light observation mode is displayed on the display apparatus 5.

Figure 8:
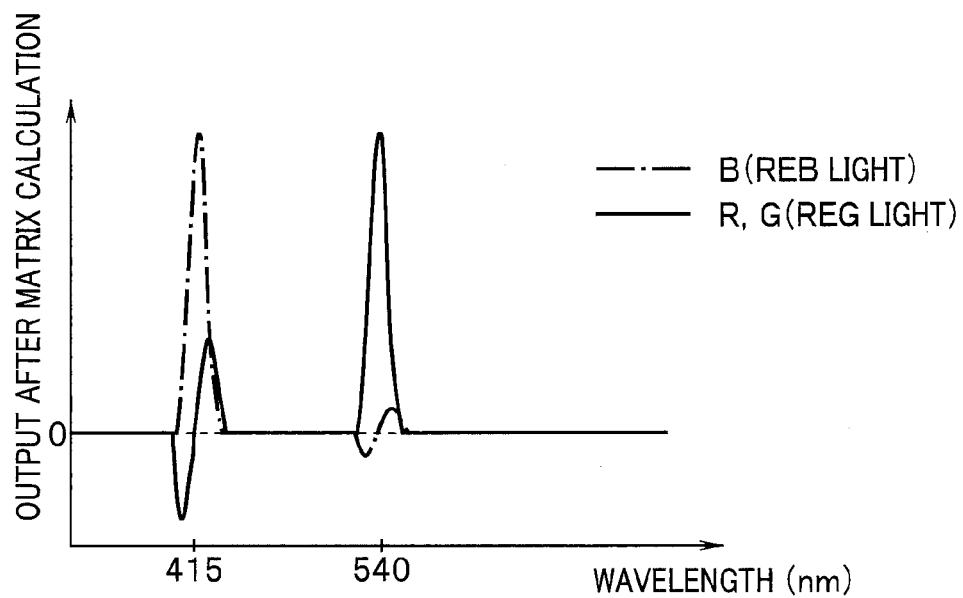
FIG. 8 is a view illustrating a different example to FIG. 5 of spectral distributions obtained as a calculation result when a calculation relating to image separation is performed using a matrix that does not have a spectral distribution correction function.

In this connection, for example, in a case where it is assumed that the matrix Ca included in the above described equation (8) and equation (10) is a unit matrix, that is, when it is assumed that the matrix MAUB does not substantially have a spectral distribution correction function, by performing a calculation using the matrix MAUB, output values of the signals of the respective color components having the spectral distributions shown in FIG. 8 are obtained. FIG. 8 is a view that illustrates an example of spectral distributions obtained as a calculation result when a calculation relating to image separation was performed using a matrix that does not have a spectral distribution correction function, which is different to the example illustrated in FIG. 5.

According to the spectral distribution of the B component shown in FIG. 8, apart from a wavelength band component corresponding to the REB light as light of the blue region having a peak wavelength in the vicinity of 415 nm, a clear fluctuation in the output value also arises in a wavelength band component corresponding to the REG light, that is, it is found that a wavelength component of the REB light is not appropriately separated.

Further, according to the spectral distribution of the G component shown in FIG. 8, apart from a wavelength band component corresponding to the REG light as light of the green region having a peak wavelength in the vicinity of 540 nm, a clear fluctuation in the output value also arises in a wavelength band component corresponding to the REB light, that is, it is found that a wavelength component of the REG light is not appropriately separated.

Figure 9:
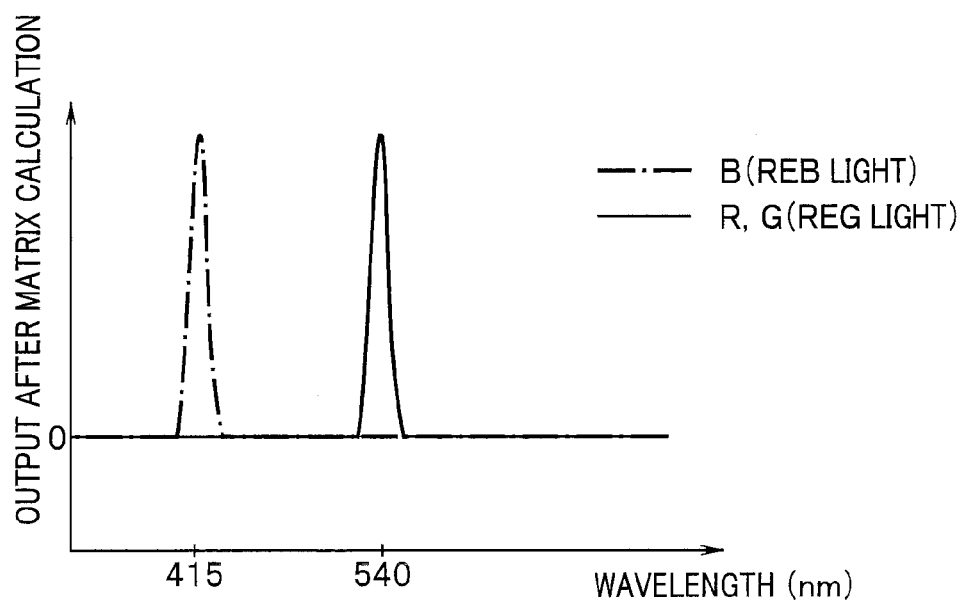
FIG. 9 is a view illustrating a different example to FIG. 6 of spectral distributions obtained as a calculation result when a calculation relating to image separation is performed using a matrix having a spectral distribution correction function.

In contrast, according to the first modification, by performing a calculation using the matrix MAUB having a spectral distribution correction function, for example, output values of signals of respective color components having the spectral distributions shown in FIG. 9 are obtained. FIG. 9 is a view illustrating an example of spectral distributions obtained as a calculation result when a calculation relating to image separation is performed using a matrix having a spectral distribution correction function, which is different to the example illustrated in FIG. 6.

According to the spectral distribution of the B component shown in FIG. 9, a clear fluctuation does not arise in an output value of another wavelength band component other than a wavelength band component corresponding to the REB light as light of the blue region having a peak wavelength in the vicinity of 415 nm, that is, the wavelength component of the REB light is appropriately separated.

Further, according to the spectral distribution of the G component shown in FIG. 9, a clear fluctuation does not arise in an output value of another wavelength band component other than a wavelength band component corresponding to the REG light as light of the green region having a peak wavelength in the vicinity of 540 nm, that is, it is found that the wavelength component of the REG light is appropriately separated.

Therefore, according to the first modification, an image including a plurality of color components obtained by a simultaneous image pickup method can be favorably separated into images for respective wavelength band components that are mutually independent.

Figure 10:
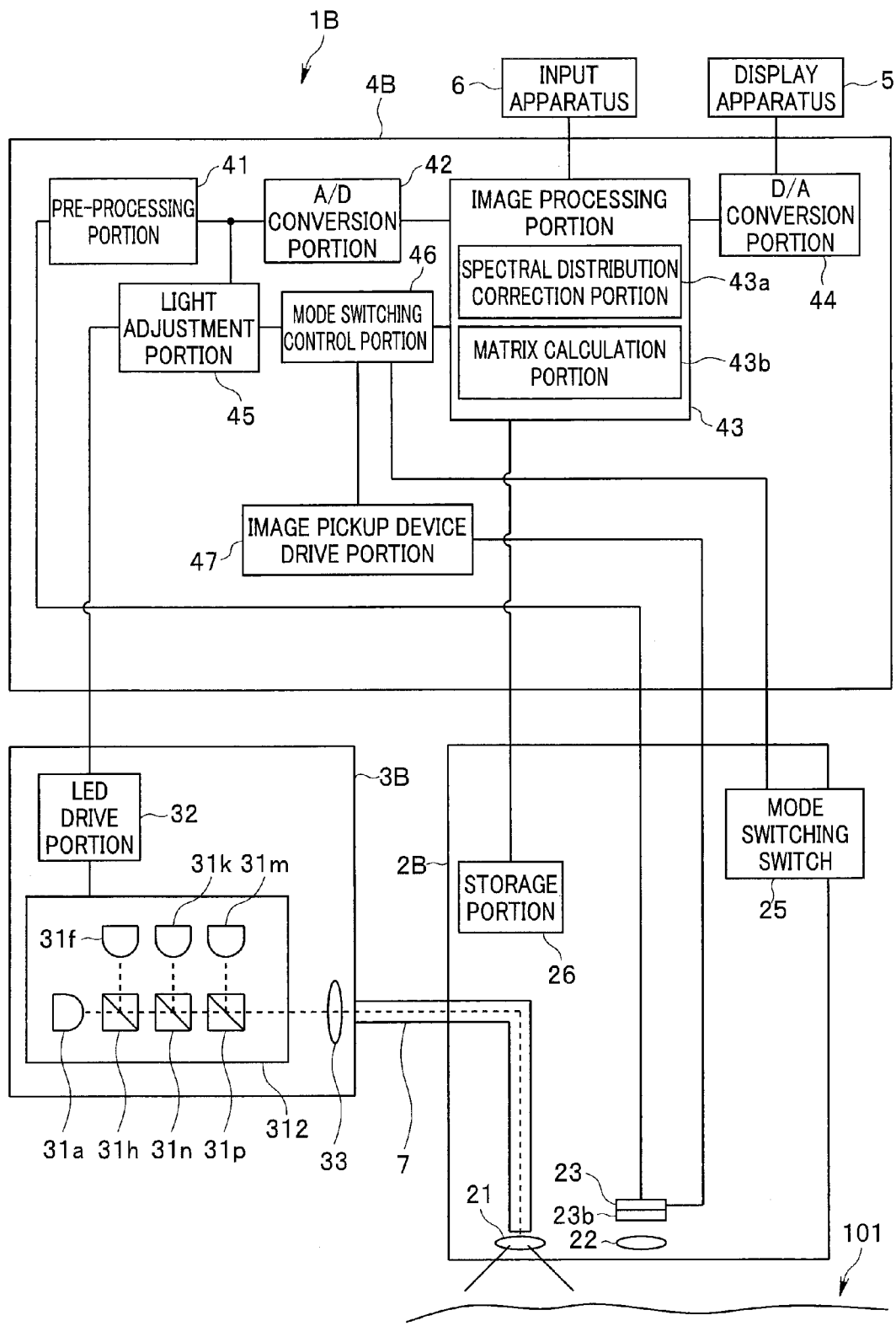
FIG. 10 is a view illustrating a configuration of main components of an endoscope apparatus according to a second modification of the embodiment of the present invention.

The matrix C and matrix MAUA that are acquired according to the present embodiment are not limited to matrices in which each coefficient is set so as to correspond to FL light and REF light as return light that is generated in the fluorescence observation mode. For example, in the matrix C and matrix MAUA, each coefficient may also be set so as to correspond to red narrow-band light and green narrow-band light as return light (reflected light) that is generated in a deep-layer blood vessel observation mode for observing a blood vessel present in an intermediate layer of biological mucosa and also a thick blood vessel present at a deeper position (hereunder, also referred to as "deep layer") than an intermediate layer of biological mucosa. A specific example of such a case will be described hereunder. FIG. 10 is a view that illustrates a configuration of main components of an endoscope apparatus according to a second modification of the embodiment of the present invention. Note that, in the following description, for brevity, a detailed description relating to portions to which the configuration and the like that is already described in relation to the endoscope apparatus 1 can be applied is omitted, and the description mainly relates to portions having a different configuration and the like to the endoscope apparatus 1.

As shown in FIG. 10, an endoscope apparatus 1B includes: a scope 2B having a configuration in which, relative to the configuration of the scope 2, the filter switching apparatus 24 is omitted and a color filter 23b is provided in place of the color filter 23a; a light source apparatus 3B having a configuration in which, relative to the configuration of the light source apparatus 3, an LED light source portion 312 is provided in place of the LED light source portion 31; and a processor 4B having a configuration in which, relative to the configuration of the processor 4, the filter switching control portion 48 is omitted.

Figure 11:
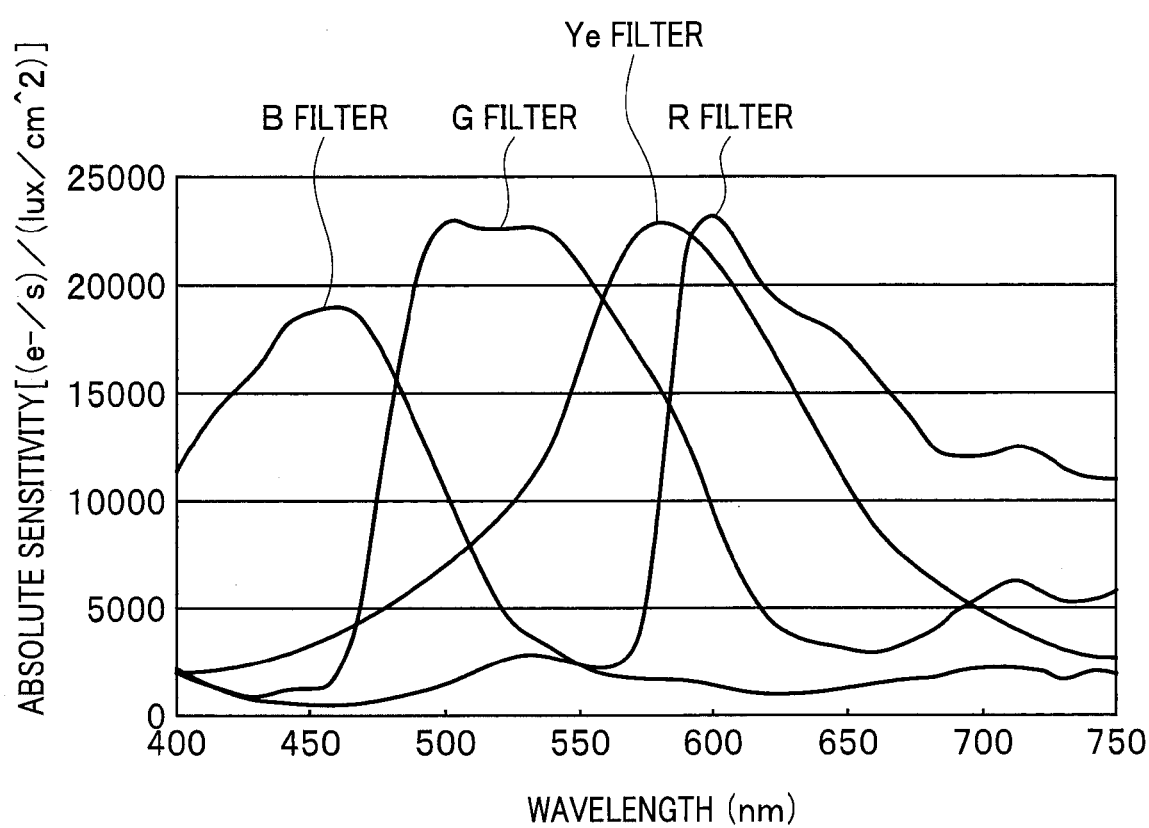
FIG. 11 is a view illustrating an example of spectral sensitivity characteristics of an R filter, a G filter, a B filter, and a Ye filter provided in a color filter of the endoscope apparatus illustrated in FIG. 10.

The color filter 23b of the scope 2B is configured as a color filter for four primary colors. More specifically, the color filter 23b of the scope 2B is formed by arranging a plurality of R (red) filters, G (green) filters, B (blue) filters, and Ye (yellow) filters that are respectively provided with predetermined spectral sensitivity characteristics (optical characteristics) at positions corresponding to respective pixels of the image pickup device 23. Note that in the present embodiment, it is assumed that, for example, R filters, G filters, B filters, and Ye filters having the spectral sensitivity characteristics shown in FIG. 11, for example, respectively, are provided in the color filter 23b. FIG. 11 is a view illustrating an example of the spectral sensitivity characteristics of the R filters, G filters, B filters, and Ye filters provided in the color filter of the endoscope apparatus shown in FIG. 10.

The R filter of the color filter 23b is configured to have spectral sensitivity characteristics (optical characteristics) such that, similarly to the R filter of the color filter 23a, transmittance in a range from a red region to a near-infrared region is relatively higher than transmittances in the other wavelength bands (see FIG. 11).

The G filter of the color filter 23b is configured to have spectral sensitivity characteristics (optical characteristics) such that, similarly to the G filter of the color filter 23a, transmittance in a green region is relatively higher than transmittances in the other wavelength bands (see FIG. 11).

The B filter of the color filter 23b is configured to have spectral sensitivity characteristics (optical characteristics) such that, similarly to the B filter of the color filter 23a, transmittance in a blue region is relatively higher than transmittances in the other wavelength bands (see FIG. 11).

The Ye filter of the color filter 23b is configured to have spectral sensitivity characteristics (optical characteristics) such that transmittance in a yellow region is relatively higher than transmittances in the other wavelength bands (see FIG. 11).

The mode switching switch 25 of the scope 2B is configured to be capable of issuing an instruction for switching the observation mode of the endoscope apparatus 1B to any single observation mode selected from the white light observation mode and the deep-layer blood vessel observation mode in accordance with an operation by a surgeon or the like.

The LED light source portion 312 is configured to include the LED 31a that emits WB light that is wide-band light, the LED 31f that emits NBG light that is light with which blood vessels present in an intermediate layer in biological mucosa can be observed, an LED 31k that emits NBR1 light that is light with which blood vessels present in a deep layer of biological mucosa can be observed, an LED 31m that emits NBR2 light that is light with which blood vessels present in a deep layer of biological mucosa can be observed, the optical element 31h, an optical element 31n, and an optical element 31p.

The LED 31f is configured to be capable of emitting narrow band light whose center wavelength is set, for example, to 540 nm as the NBG light.

The LED 31k is configured to be capable of emitting narrow band light whose center wavelength is set, for example, to 630 nm as the NBR1 light.

The LED 31m is configured to be capable of emitting narrow band light whose center wavelength is set, for example, to 650 nm as the NBR2 light.

The optical element 31h is constituted by, for example, a half mirror, and has optical characteristics such that the WB light emitted from the LED 31a is transmitted to the optical element 31n side and the NBG light emitted from the LED 31f is reflected toward the optical element 31n side.

The optical element 31n is constituted by, for example, a half mirror, and has optical characteristics such that the WB light and NBG light emitted via the optical element 31h are transmitted to the optical element 31p side, and the NBR1 light emitted from the LED 31k is reflected toward the optical element 31p side.

The optical element 31p is constituted by, for example, a half mirror, and has optical characteristics such that the WB light, NBG light, and NR1 light emitted via the optical element 31n are transmitted to the condensing optical system 33 side, and the NBR2 light emitted from the LED 31m is reflected toward the condensing optical system 33 side.

The spectral distribution correction portion 43a of the processor 4B acquires a matrix Cb having a spectral distribution correction function by performing processing based on predetermined information outputted from the storage portion 26 accompanying connection of the scope 2B and the processor 4B.

The matrix calculation portion 43b of the processor 4B performs processing based on predetermined information outputted from the storage portion 26 accompanying connection of the scope 2B and the processor 4B, and the matrix Cb acquired by the spectral distribution correction portion 43a to thereby perform calculation processing for acquiring a matrix MAUC that has both a spectral distribution correction function and an image separation function.

Further, the matrix calculation portion 43b of the processor 4B performs calculations by applying the matrix MAUC to image data that is inputted to the image processing portion 43 in the deep-layer blood vessel observation mode, and also performs processing to allocate the image data of each wavelength band component obtained as a result of the calculations to an R channel, a G channel, and a B channel of the display apparatus 5.

Upon detecting that the endoscope apparatus 1B has been switched to the white light observation mode based on the mode switching signal outputted from the mode switching control portion 46 and the image pickup signal outputted from the pre-processing portion 41, the light adjustment portion 45 of the processor 4B outputs to the LED drive portion 32 a light adjustment signal for turning off the LED 31f, the LED 31k, and the LED 31m and for also causing the LED 31a to emit light at an intensity appropriate for observation in the white light observation mode. Further, upon detecting that the endoscope apparatus 1 has been switched to the deep-layer blood vessel observation mode based on the mode switching signal outputted from the mode switching control portion 46 and the image pickup signal outputted from the pre-processing portion 41, the light adjustment portion 45 of the processor 4B outputs to the LED drive portion 32 a light adjustment signal for turning off the LED 31a and for also causing the LED 31f, the LED 31k, and the LED 31m to simultaneously emit light at an intensity appropriate for observation in the deep-layer blood vessel observation mode.

Upon detecting that the endoscope apparatus 1B has been switched to the white light observation mode based on the mode switching signal outputted from the mode switching control portion 46 and the image pickup signal outputted from the pre-processing portion 41, the light adjustment portion 45 of the processor 4B outputs to the LED drive portion 32 a light adjustment signal for turning off the LED 31f, the LED 31k, and the LED 31m and for also causing the LED 31a to emit light at an intensity appropriate for observation in the white light observation mode. Further, upon detecting that the endoscope apparatus 1B has been switched to the deep-layer blood vessel observation mode based on the mode switching signal outputted from the mode switching control portion 46 and the image pickup signal outputted from the pre-processing portion 41, the light adjustment portion 45 of the processor 4B outputs to the LED drive portion 32 a light adjustment signal for turning off the LED 31a and for also causing the LED 31f, the LED 31k, and the LED 31m to simultaneously emit light at an intensity appropriate for observation in the deep-layer blood vessel observation mode.

Next, operations of the endoscope apparatus 1B according to the second modification will be described. Note that since operations and the like of the respective portions in a case where the observation mode of the endoscope apparatus 1B is set to the white light observation mode are the same as in the case of the endoscope apparatus 1, a description of those operations is omitted hereunder.

The user performs an operation to insert the scope 2B while observing the observed image in the white light observation mode that is displayed on the display apparatus 5, and thereby places the distal end portion of the scope 2B in the vicinity of the desired site to be observed 101 inside the subject. In that state, the user or the like operates the mode switching switch 25 to issue an instruction for switching the observation mode of the endoscope apparatus 1B to the deep-layer blood vessel observation mode.

Upon detecting that an instruction for switching the observation mode of the endoscope apparatus 1B to the deep-layer blood vessel observation mode was issued at the mode switching switch 25, the mode switching control portion 46 outputs a mode switching signal for causing operations corresponding to the deep-layer blood vessel observation mode to be performed to the image processing portion 43, the light adjustment portion 45, and the image pickup device drive portion 47.

Based on a light adjustment signal outputted from the light adjustment portion 45, the LED drive portion 32 turns off the LED 31a of the LED light source portion 31 and also causes the LED 31f, the LED 31k, and the LED 31m to simultaneously emit light at an intensity appropriate for observation in the deep-layer blood vessel observation mode.

As a result of such operations of the LED drive portion 32, in the deep-layer blood vessel observation mode, NBG light, NBR1 light, and NBR2 light supplied from the light source apparatus 3B is emitted to the site to be observed 101 via the light guide 7 and the illumination optical system 21, and mixed light of REG light that is reflected light of the NBG light, RERA light that is reflected light of the NBR1 light, and RERB light that is reflected light of the NBR2 light is impinged on the objective optical system 22 as return light from the site to be observed 101.

On the other hand, the image pickup device 23 receives light that has passed through the R filter of the color filter 23b, light that has passed through the G filter of the color filter 23b, light that has passed through the B filter of the color filter 23b, and light that has passed through the Ye filter of the color filter 23b, respectively, and generates and outputs an image pickup signal obtained by picking up images of the respective lights that were received.

The pre-processing portion 41 performs processing such as signal amplification and noise removal with respect to the image pickup signal outputted from the scope 2B, and outputs the resulting image pickup signal that underwent the processing to the A/D conversion portion 42.

The A/D conversion portion 42 converts an analog image pickup signal outputted from the pre-processing portion 41 to digital image data, and outputs the digital image data to the image processing portion 43. Through such processing of the A/D conversion portion 42, image data is generated which includes a red color component RD2, a green color component GD2, a blue color component BD2, and a yellow color component YeD corresponding to the intensity of the REG light, the RERA light, and the RERB light received at (the image pickup surface of) the image pickup device 23.

Upon detecting that the endoscope apparatus 1B has been switched to the deep-layer blood vessel observation mode based on the mode switching signal outputted from the mode switching control portion 46, the image processing portion 43 operates so as to cause the matrix calculation portion 43b to execute calculation processing using the matrix MAUC.

Here, processing relating to acquisition of the matrix MAUC that has both a spectral distribution correction function and an image separation function will be described. Note that it is assumed that the processing relating to acquisition of the matrix MAUC is executed at an arbitrary timing before the observation mode of the endoscope apparatus 1B is switched to the deep-layer blood vessel observation mode.

Upon detecting that the scope 2B and the processor 4B have been connected, as predetermined information to be used in the calculation processing for acquiring the matrix MAUC, the storage portion 26, for example, outputs information showing the spectral sensitivity characteristics of the respective filters (R filter, G filter, and B filter) of the color filter 23b and information showing the spectral distribution of the REG light, the RERA light, and the RERB light that are the return light emitted from the object in the deep-layer blood vessel observation mode to the image processing portion 43 of the processor 4B.

Based on the information showing the spectral sensitivity characteristics of the image pickup device 23 that includes the respective filters (R filter, G filter, B filter, and Ye filter) of the color filter 23b and the information showing the spectral distributions of the REG light, the RERA light and the RERB light emitted from the object in the deep-layer blood vessel observation mode, the spectral distribution correction portion 43a acquires spectral distributions of the red color component RD2, the green color component GD2, the blue color component BD2, and the yellow color component YeD that are included in image data that is inputted into the image processing portion 43 in the deep-layer blood vessel observation mode.

Further, by the method mentioned previously (method that makes a peak value of a signal intensity for each peak wavelength 1.0, respectively), the spectral distribution correction portion 43a normalizes the spectral distributions of the red color component RD2, the green color component GD2, the blue color component BD2, and the yellow color component YeD acquired as described above. By performing this normalization, differences between the spectral distributions of the respective color components become evident.

Further, the spectral distribution correction portion 43a acquires a matrix Cb of 4 rows and 4 columns in which the respective coefficients are set so as to make the shapes of the normalized spectral distributions match each other.

The matrix Cb acquired through the processing of the spectral distribution correction portion 43a that is described above has a spectral distribution correction function that is capable of correcting the spectral distributions of the respective color components (red color component RD2, green color component GD2, blue color component BD2, and yellow color component YeD) before normalization, that is, correcting the shapes of the spectral distributions of the respective color components (red color component RD2, green color component GD2, blue color component BD2, and yellow color component YeD) of image data generated based on the REG light, the RERA light, and the RERB light received on the image pickup surface of the image pickup device 23 when operating in the deep-layer blood vessel observation mode so as to become similar shapes to each other.

On the other hand, the matrix calculation portion 43b acquires a matrix MAUB by performing the following processing and the like based on the matrix Cb of 4 rows and 4 columns acquired by the processing of the spectral distribution correction portion 43a as described above, information showing the spectral sensitivity characteristics of the respective filters (R filter, G filter, B filter, and Ye filter) of the color filter 23b, and information showing the spectral distributions of the REG light, the RERA light, and the RERB light emitted from the object in the deep-layer blood vessel observation mode.

First, based on the information showing the spectral sensitivity characteristics of the respective filters (R filter, G filter, B filter and Ye filter) of the color filter 23b, and the information showing the spectral distributions of the REG light, RERA light, and RERB light emitted from the object in the deep-layer blood vessel observation mode, the matrix calculation portion 43b defines a matrix corresponding to the intensity of the red color component RD2, the green color component GD2, the blue color component BD2, and the yellow color component YeD included in image data $I_{RGBYe}$ that is inputted to the image processing portion 43 in the deep-layer blood vessel observation mode, as shown in the following equation (13). Note that, in the following equation (13), it is assumed that $R_{REG}$ represents the intensity of the red color component based on the wavelength component of the REG light received via the R filter of the color filter 23b, $G_{REG}$ represents the intensity of the green color component based on the wavelength component of the REG light received via the G filter of the color filter 23b, $B_{REG}$ represents the intensity of the blue color component based on the wavelength component of the REG light received via the B filter of the color filter 23b, and $Ye_{REG}$ represents the intensity of the blue color component based on the wavelength component of the REG light received via the Ye filter of the color filter 23b. Further, in the following equation (13), it is assumed that $R_{RERA}$ represents the intensity of the red color component based on the wavelength component of the RERA light received via the R filter of the color filter 23b, $G_{RERA}$ represents the intensity of the green color component based on the wavelength component of the RERA light received via the G filter of the color filter 23b, $B_{RERA}$ represents the intensity of the blue color component based on the wavelength component of the RERA light received via the B filter of the color filter 23b, and $Ye_{RERA}$ represents the intensity of the blue color component based on the wavelength component of the RERA light received via the Ye filter of the color filter 23b. Furthermore, in the following equation (13), it is assumed that $R_{RERB}$ represents the intensity of the red color component based on the wavelength component of the RERB light received via the R filter of the color filter 23b, $G_{RERB}$ represents the intensity of the green color component based on the wavelength component of the RERB light received via the G filter of the color filter 23b, $B_{RERB}$ represents the intensity of the blue color component based on the wavelength component of the RERB light received via the B filter of the color filter 23b, and $Ye_{RB}$ represents the intensity of the blue color component based on the wavelength component of the RERB light received via the Ye filter of the color filter 23b.

$$I_{RGBYe} = \begin{pmatrix} R_{REG} & R_{RERA} & R_{RERB} \\ G_{REG} & G_{RERA} & G_{RERB} \\ B_{REG} & B_{RERA} & B_{RERB} \\ Ye_{REG} & Ye_{RERA} & Ye_{RERB} \end{pmatrix} \quad (13)$$

Here, when a matrix for separating image data of three mutually independent color components from the respective color components included in the image data inputted to the image processing portion 43 in the deep-layer blood vessel observation mode is set as MAUC, and a matrix representing the image data of the three color components after separation is set as S', the relations shown in the following equations (14) and (15) are established.

$$S' = MAUC \cdot Cb \cdot I_{RGBYe} \quad (14)$$

$$S' = \begin{pmatrix} 1 & 0 & 0 \\ 0 & 1 & 0 \\ 0 & 0 & 1 \end{pmatrix} \quad (15)$$

Further, the matrix calculation portion 43b determines the matrix MAUC of 3 rows and 4 columns by performing the calculation in the following equation (16) based on the above described equations (14) and (15). Note that it is assumed that $(Cb \cdot I_{RGBYe})^+$ in the following equation (16) represents a pseudo-inverse matrix of the product of the matrix Cb of 4 rows and 4 columns and a matrix $I'_{RGB}$ of 4 rows and 3 columns as represented by the above described equation (13). Note that, it is assumed that M51 to M54, M61 to M64 and M71 to M74 in the following equation (16) represent arbitrary coefficients, respectively.

$$MAUC = S' \cdot (Cb \cdot I_{RGBYe})^+ \quad (16)$$
$$= \begin{pmatrix} M51 & M52 & M53 & M54 \\ M61 & M62 & M63 & M64 \\ M71 & M72 & M73 & M74 \end{pmatrix}$$

According to the processing using the matrix MAUC determined through the calculation of equation (16) above, it is possible to separate first image data ING including only a color component corresponding to a wavelength component of the REG light, second image data INR1 including only a color component corresponding to a wavelength component of the RERA light, and third image data INR2 including only a color component corresponding to a wavelength component of the RERB light from the respective color components included in the image data inputted to the image processing portion 43 in the deep-layer blood vessel observation mode.

That is, the matrix calculation portion 43b acquires a matrix MAUC expressed as the above equation (16) by performing the processing and the like described above based on the matrix Cb of 4 rows and 4 columns, information showing the spectral sensitivity characteristics of the respective filters (R filter, G filter, B filter, and Ye filter) of the color filter 23b, and information showing the spectral distributions of the REG light, the RERA light, and the RERB light emitted from the object in the deep-layer blood vessel observation mode.

The matrix calculation portion 43b then performs calculations by applying the previously acquired matrix MAUC to the red color component RD2, the green color component GD2, the blue color component BD2 and the yellow color component YeD included in the image data that is inputted to the image processing portion 43 in the deep-layer blood vessel observation mode, and thereby acquires the image data ING including only a color component corresponding to a wavelength component of the REG light, the image data INR1 including only a color component corresponding to a wavelength component of the RERA light, and the image data INR2 including only a color component corresponding to a wavelength component of the RERB light.

Further, the matrix calculation portion 43b allocates the image data ING, the image data INR1, and the image data iNR2 acquired as described above to an arbitrary color channel (R, G, or B channel), respectively, of the display apparatus 5.

Thereafter, the image processing portion 43 executes processing such as gamma correction and edge enhancement with respect to the image data allocated to the respective color channels of R, G and B of the display apparatus 5 through the processing of the matrix calculation portion 43b, and outputs the image data to the D/A conversion portion 44.

The display apparatus 5 then displays an image of the object corresponding to the video signal outputted via the D/A conversion portion 44.

That is, as a result of the above-described operations and the like being performed in the deep-layer blood vessel observation mode, an observed image corresponding to the deep-layer blood vessel observation mode is displayed on the display apparatus 5.

Figure 12:
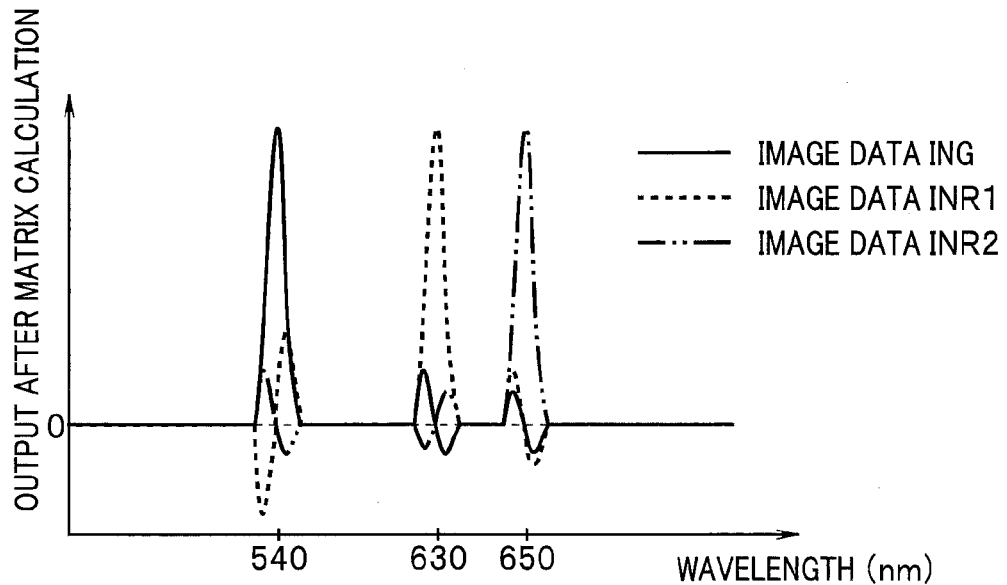
FIG. 12 is a view illustrating a different example to the examples in FIG. 5 and FIG. 8 of spectral distributions obtained as a calculation result when a calculation relating to image separation is performed using a matrix that does not have a spectral distribution correction function.

In this connection, for example, in a case where it is assumed that the matrix Cb included in the above described equation (14) and equation (16) is a unit matrix, that is, when it is assumed that the matrix MAUC does not substantially have a spectral distribution correction function, by performing a calculation using the matrix MAUC, output values of the signals of the respective color components having the spectral distributions shown in FIG. 12 are obtained. FIG. 12 is a view that illustrates an example of spectral distributions obtained as a calculation result when a calculation relating to image separation was performed using a matrix that does not have a spectral distribution correction function, which is different to the examples illustrated in FIG. 5 and FIG. 8.

According to the spectral distribution of the image data ING shown in FIG. 12, apart from a wavelength band component corresponding to the REG light as light of the green region having a peak wavelength in the vicinity of 540 nm, a clear fluctuation in the output value also arises in a wavelength band component corresponding to the RERA light and the RERB light, that is, it is found that a wavelength band component of the REG light is not appropriately separated.

Further, according to the spectral distribution of the image data INR1 shown in FIG. 12, apart from a wavelength band component corresponding to the RERA light as light of the red region having a peak wavelength in the vicinity of 630 nm, a clear fluctuation in the output value also arises in a wavelength band component corresponding to the REG light and the RERB light, that is, it is found that a wavelength band component of the RERA light is also not appropriately separated.

Further, according to the spectral distribution of the image data INR2 shown in FIG. 12, apart from a wavelength band component corresponding to the RERB light as light of the red region having a peak wavelength in the vicinity of 650 nm, a clear fluctuation in the output value also arises in a wavelength band component corresponding to the REG light and the RERA light, that is, it is found that a wavelength band component of the RERB light is also not appropriately separated.

Figure 13:
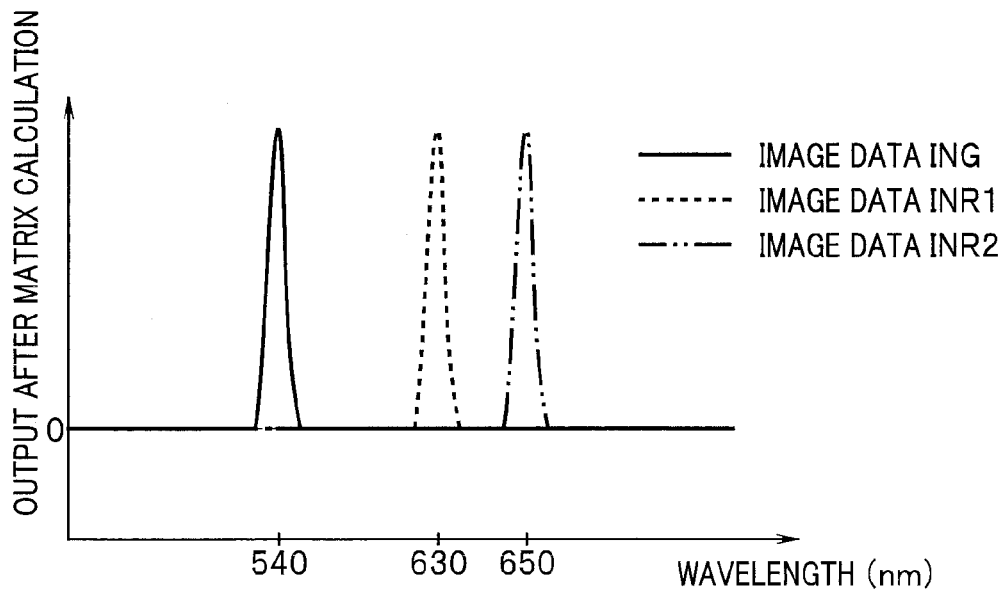
FIG. 13 is a view illustrating a different example to the examples in FIG. 6 and FIG. 9 of spectral distributions obtained as a calculation result when a calculation relating to image separation is performed using a matrix having a spectral distribution correction function.

In contrast, according to the second modification, by the performance of a calculation using the matrix MAUC having a spectral distribution correction function, for example, output values of signals of respective color components having the spectral distributions as shown in FIG. 13 are obtained. FIG. 13 is a view illustrating an example of spectral distributions obtained as a calculation result when a calculation relating to image separation is performed using a matrix having a spectral distribution correction function, which is different to the examples illustrated in FIG. 6 and FIG. 9.

According to the spectral distribution of the image data ING shown in FIG. 13, a clear fluctuation does not arise in the output value of another wavelength band component other than a wavelength band component corresponding to the REG light as light of the green region having a peak wavelength in the vicinity of 540 nm, that is, it is found that the wavelength band component of the REG light is appropriately separated.

Further, according to the spectral distribution of the image data INR1 shown in FIG. 13, a clear fluctuation does not arise in the output value of another wavelength band component other than a wavelength band component corresponding to the RERA light as light of the red region having a peak wavelength in the vicinity of 630 nm, that is, it is found that the wavelength component of the RERA light is appropriately separated.

Further, according to the spectral distribution of the image data INR2 shown in FIG. 13, a clear fluctuation does not arise in the output value of another wavelength band component other than a wavelength band component corresponding to the RERB light as light of the red region having a peak wavelength in the vicinity of 650 nm, that is, it is found that the wavelength component of the RERB light is appropriately separated.

Therefore, according to the second modification, an image including a plurality of color components obtained by a simultaneous image pickup method can be favorably separated into images for respective wavelength band components that are mutually independent.

Note that the present invention is not limited to the above described embodiment, and naturally various changes and applications are possible within a range that does not depart from the spirit and scope of the present invention.

What is claimed is:

1. An endoscope apparatus, comprising:
   a light source that generates illuminating light for simultaneously generating light including a first wavelength band as return light from an object and light including a second wavelength band different from the first wavelength band;
   an imager connected to an endoscope which is connected to the light source, the imager comprising a plurality of pixels, wherein the imager is configured to receive the return light from the object and to generate image pickup signals for the respective plurality of pixels;
   a color filter comprising a plurality of filters each having a peak of transmittance in a different color, wherein each of the plurality of filters is arranged for each of the plurality of pixels of the imager; and
   a processor comprising hardware, wherein the processor is configured to implement:
   a corrector that, based on information relating to a spectral distribution of the return light that is generated from the object and information showing spectral sensitivity of the color filter, sets a correction matrix so that spectral distributions of the first wavelength band included in image pickup signals for respective different colors generated by the imager have a similar shape to each other; and
   a matrix calculator that:
   receives inputs of the image pickup signals for the respective different colors generated by the imager and the correction matrix set by the corrector;
   generates, based on the information relating to the spectral distribution of the return light that is generated from the object and the information showing the spectral sensitivity of the color filter, a matrix with intensities of components in the first wavelength band for the respective different colors and intensities of components in the second wavelength band for the respective different colors as parameters, the components in the first wavelength band and the components in the second wavelength band having passed through the plurality of filters comprising the color filter;

generates a color separation matrix by performing a matrix calculation for multiplying the matrix with intensities of components in the first wavelength band for the respective different colors and intensities of components in the second wavelength band for the respective different colors as parameters, by the correction matrix inputted from the corrector;

performs a matrix calculation on the image pickup signals for the respective different colors which are inputted from the imager, using the color separation matrix; and performs a calculation for separating image pickup signals corresponding to the first wavelength band and the image pickup signals corresponding to the second wavelength band.

2. The endoscope apparatus according to claim 1, further comprising:

a memory that is provided in the endoscope, the memory being configured to store the information showing the spectral sensitivity of the color filter and output the information showing the spectral sensitivity of the color filter to the corrector.

3. The endoscope apparatus according to claim 1, further comprising:

a controller that switches an observation mode between a white light observation mode in which observation is performed with white light and a special light observation mode in which observation is performed with special light different from the white light, wherein the matrix calculator does not perform the matrix calculation using the color separation matrix when the observation mode is switched to the white light observation mode with the controller, and performs the matrix calculation using the color separation matrix when the observation mode is switched to the special light observation mode with the controller.

* * * * *